(12) United States Patent
Lubenau

(10) Patent No.: US 10,293,037 B2
(45) Date of Patent: *May 21, 2019

(54) DNA VACCINE FOR USE IN PANCREATIC CANCER PATIENTS

(71) Applicant: Vaximm AG, Basel (CH)

(72) Inventor: Heinz Lubenau, Neustadt an der Weinstrasse (DE)

(73) Assignee: VAXIMM AG (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/994,766

(22) Filed: May 31, 2018

(65) Prior Publication Data

US 2019/0008936 A1 Jan. 10, 2019

Related U.S. Application Data

(63) Continuation of application No. 15/158,387, filed on May 18, 2016, now abandoned, which is a continuation of application No. 14/409,434, filed as application No. PCT/EP2013/001882 on Jun. 26, 2013, now Pat. No. 9,415,098.

(30) Foreign Application Priority Data

Jul. 5, 2012 (EP) .................................... 12004995

(51) Int. Cl.
| | |
|---|---|
| *A61K 39/112* | (2006.01) |
| *C07K 14/71* | (2006.01) |
| *A61K 31/7068* | (2006.01) |
| *A61K 39/00* | (2006.01) |
| *C12N 1/20* | (2006.01) |
| *C12N 1/36* | (2006.01) |
| *C12R 1/42* | (2006.01) |

(52) U.S. Cl.
CPC ...... *A61K 39/0011* (2013.01); *A61K 31/7068* (2013.01); *A61K 39/0275* (2013.01); *C07K 14/71* (2013.01); *C12N 1/20* (2013.01); *C12N 1/36* (2013.01); *C12R 1/42* (2013.01); *A61K 2039/522* (2013.01); *A61K 2039/523* (2013.01); *A61K 2039/53* (2013.01); *A61K 2039/542* (2013.01); *A61K 2039/545* (2013.01); *A61K 2039/57* (2013.01); *Y02A 50/484* (2018.01)

(58) Field of Classification Search
None
See application file for complete search history.

(56) References Cited

U.S. PATENT DOCUMENTS

| | | | |
|---|---|---|---|
| 7,622,115 | B2 | 11/2009 | Fyfe et al. |
| 9,415,098 | B2 * | 8/2016 | Lubenau ............ A61K 39/0011 |
| 2015/0165011 | A1 | 6/2015 | Lubenau |

FOREIGN PATENT DOCUMENTS

| | | |
|---|---|---|
| CN | 1649622 A | 8/2005 |
| GB | 2 248 241 A | 4/1992 |
| WO | WO-03/073995 A2 | 9/2003 |
| WO | WO-2013/091898 A1 | 6/2013 |

OTHER PUBLICATIONS

Schmitz-Winnenthal, F.H. et al. (2015) "Anti-angiogenic activity of VXM01, an oral Tcell vaccine against VEGF receptor 2, in patients with advanced pancreatic cancer: A randomized, placebo-controlled, phase 1 trial," OncoImmunology 4(4):e1001217.
Allegra, C.J. et al. (2011) "Phase III Trial Assessing Bevacizumab in Stages II and III Carcinoma of the Colon: Results of NSABP Protocol C-08," J Clin Oncol 29(1):11-16.
Augustin, H.G. (1998) "Antiangiogenic tumour therapy: will it work?" TiPS 19:216-222.
Burger, R.A. et al. (2011) "Incorporation of Bevacizumab in the Primary Treatment of Ovarian Cancer," N Engl J Med 365(26):2473-2483.
Focus article (2011) "Vaccination against pancreatic cancer: Hope for oral vaccination against cancer", retrieved from http://www.focus.de website on Apr. 14, 2017.
Fraillery, D. et al. (2007) "*Salmonella enterica* Serovar Typhi Ty21a Expressing Human Papillomavirus Type 16 L1 as a Potential Live Vaccine against Cervical Cancer and Typhoid Fever," Clinical and Vaccine Immunology 14(10):1285-1295.
Hotz, C. et al. (2009) "Improvement of the live vaccine strain *Salmonella enterica* serovar Typhi Ty21a for antigen delivery via the hemolysin secretion system of *Escherichia coli*," International Journal of Medical Microbiology 299(2):109-119.
Houghten, R.A. et al. (1986) "Relative Importance of Position and Individual Amino Acid Residues in Peptide Antigen-Antibody Interactions: Implications in the Mechanism of Antigenic Drift and Antigenic Shift", Vaccines, Edited by Fred Brown, Cold Spring Harbor Laboratory:21-25.
International Search Report and Written Opinion of the International Searching Authority (ISA/EP) for International Application No. PCT/EP2013/001882, dated Oct. 4, 2013.
Luo, Y. et al. (2007) "FLK-1-based minigene vaccines induce T cell-mediated suppression of angiogenesis and tumor protective immunity in syngeneic BALB/c mice," Vaccine 25(8):1409-1415.
McKenna, A.J. et al. (1995) "Attenuated typhoid vaccine *Salmonella typhi* TY21a: fingerprinting and quality control," Microbiology 141:1993-2002.
Miyazawa, M. et al. (2010) "Phase I clinical trial using peptide vaccine for human vascular endothelial growth factor receptor 2 in combination with gemcitabine for patients with advanced pancreatic cancer," Cancer Science 101(2):433-439.
Niethammer, A.G. et al. (2002) "A DNA vaccine against VEGF receptor 2 prevents effective angiogenesis and inhibits tumor growth," Nature Medicine. 8(12):1369-1375.

(Continued)

*Primary Examiner* — Padmavathi Baskar
(74) *Attorney, Agent, or Firm* — Foley & Lardner LLP; Antoinette F. Konski

(57) ABSTRACT

The present invention relates to an attenuated mutant strain of *Salmonella* comprising a recombinant DNA molecule encoding a VEGF receptor protein. In particular, the present invention relate to the use of said attenuated mutant strain of *Salmonella* in cancer immunotherapy.

18 Claims, 10 Drawing Sheets

Figure 2:
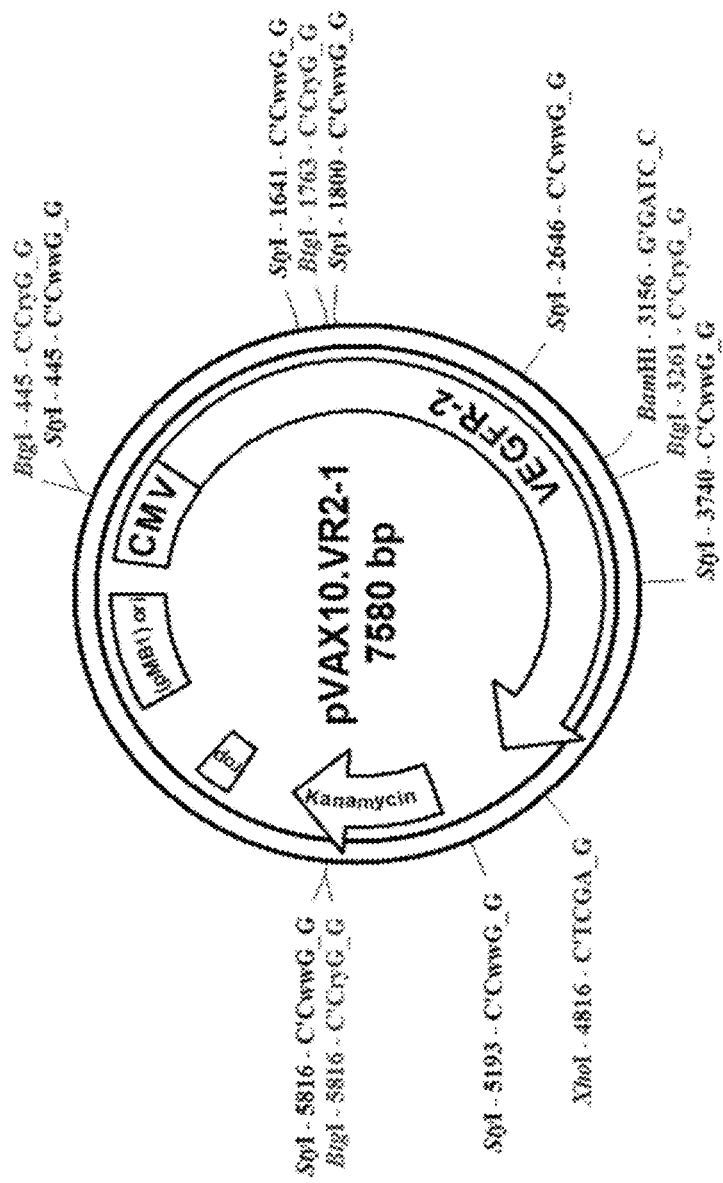

Specification includes a Sequence Listing.

(56) References Cited

OTHER PUBLICATIONS

Niethammer, A.G. et al. (2012) "Double-blind, placebo-controlled first in human study to investigate an oral vaccine aimed to elicit an immune reaction against the VEGF-Receptor 2 in patients with stage IV and locally advanced pancreatic cancer," BMC Cancer 12(1):361.
Perren, T.J. et al. (2011) "A Phase 3 Trial of Bevacizumab in Ovarian Cancer," N Engl J Med 365(26):2484-2496.
Powles, T. et al. (2011) "Sunitinib and other targeted therapies for renal cell carcinoma," British Journal of Cancer 104:741-745.
pVAX1 Catalog No. V260-20, Version C 111110, 25-0256; Invitrogen life technologies.
Reisfeld, R.A. et al. (2004) "DNA vaccines suppress tumor growth and metastases by the induction of anti-angiogenesis," Immunological Reviews 199(1):181-190.
Rini, B.I. et al. (2011) "Comparative effectiveness of axitinib versus sorafenib in advanced renal cell carcinoma (AXIS): a randomized phase 3 trial," Lancet 378:1931-1939.
Sharma, P. et al. (2011) "Novel cancer immunotherapy agents with survival benefit: recent successes and next steps," Nat Rev Cancer 11(11):805-812.
VAXIMM article (2011) "VAXIMM Starts Clinical Study of First Oral Cancer Vaccine", VAXIMM Press Release, downloaded from https://www.b3cnewswire.com on Sep. 12, 2016.
Wahdan, M.H. et al. (1982) "A Controlled Field Trial of Live *Salmonella typhi* Strain Ty 21a Oral Vaccine Against Typhoid: Three-Year Results," The Journal of Infectious Diseases 145(3):292-295.
Wahld, R. et al. (2012) "Live Oral Typhoid Vaccine Ty21a Induces Cross-Reactive Humoral Immune Responses against *Salmonella enterica* Serovar Paratyphi A and S. Paratyphi B in Humans," Clinical and Vaccine Immunology 19(6):825-834.
Yu, B. et al. (2011) "A method to generate recombinant *Salmonella typhi* Ty21a strains expressing multiple heterologous genes using an improved recombineering strategy," Applied Microbiology and Biotechnology 91(1):177-188.
Zhang, X.L. et al. (2008) "*Salmonella typhi*: from a Human Pathogen to a Vaccine Vector," Cell Mol Immunol. 5(2):91-97.
Zhou, H. et al. (2005) "T cell-mediated suppression of angiogenesis results in tumor protective immunity," Blood 106(6):2026-2032.
Zuo, S.G. et al. (2010) "Orally Administered DNA Vaccine Delivery by Attenuated *Salmonella typhimurium* Targeting Fetal Liver Kinase 1 Inhibits Murine Lewis Lung Carcinoma Growth and Metastasis," Biological & Pharmaceutical Bulletin 33(2):174-182.
Restriction Requirement for U.S. Appl. No. 14/409,434 dated Sep. 17, 2015.
Non-Final Office Action for U.S. Appl. No. 14/409,434 dated Dec. 11, 2015.
Non-Final Office Action for U.S. Appl. No. 15/158,387, dated Mar. 29, 2017.
Final Office Action for U.S. Appl. No. 15/158,387, dated Jan. 26, 2018.
Final Office Action for U.S. Appl. No. 15/158,387, dated Mar. 30, 2018.
Non-Final Office Action for U.S. Appl. No. 15/158,387, dated Apr. 6, 2018.

* cited by examiner

Figure 1:

```
                10         20         30         40         50         60
        MQSKVLLAVA LWLCVETRAA SVGLPSVSLD LPRLSIQKDI LTIKANTTLQ ITCRGQRDLD 70         80         90        100        110        120
        WLWPNNQSGS EQRVEVTECS DGLFCKTLTI PKVIGNDTGA YKCFYRETDL ASVIYVYVQD 130        140        150        160        170        180
        YRSPFIASVS DQHGVVYITE NKNKTVVIPC LGSISNLNVS LCARYPEKRF VPDGNRISWD 190        200        210        220        230        240
        SKKGFTIPSY MISYAGMVFC EAKINDESYQ SIMYIVVVVG YRIYDVVLSP SHGIELSVGE 250        260        270        280        290        300
        KLVLNCTART ELNVGIDFNW EYPSSKHQHK KLVNRDLKTQ SGSEMKKFLS TLTIDGVTRS 310        320        330        340        350        360
        DQGLYTCAAS SGLMTKKNST FVRVHEKPFV AFGSGMESLV EATVGERVRI PAKYLGYPPP 370        380        390        400        410        420
        EIKWYKNGIP LESNHTIKAG HVLTIMEVSE RDTGNYTVIL TNPISKEKQS HVVSLVVYVP 430        440        450        460        470        480
        PQIGEKSLIS PVDSYQYGTT QTLTCTVYAI PPPHHIHWYW QLEEECANEP SQAVSVTNPY 490        500        510        520        530        540
        PCEEWRSVED FQGGNKIEVN KNQFALIEGK NKTVSTLVIQ AANVSALYKC EAVNKVGRGE 550        560        570        580        590        600
        RVISFHVTRG PEITLQPDMQ PTEQESVSLW CTADRSTFEN LTWYKLGPQP LPIHVGELPT 610        620        630        640        650        660
        PVCKNLDTLW KLNATMFSNS TNDILIMELK NASLQDQGDY VCLAQDRKTK KRHCVVRQLT 670        680        690        700        710        720
        VLERVAPTIT GNLENQTTSI GESIEVSCTA SGNPPPQIMW FKDNETLVED SGIVLKDGNR.
```

Figure 1 (contd.)

```
        730        740        750        760        770        780
NLTIRRVRKE DEGLYTCQAC SVLGCAKVEA FFIIEGAQEK TNLEIIILVG TAVIAMFFWL 790        800        810        820        830        840
LLVIILRTVK RANGGELKTG YLSIVMDPDE LPLDEHCERL PYDASKWEFP RDRLKLGKPL 850        860        870        880        890        900
GRGAFGQVIE ADAFGIDKTA TCRTVAVKML KEGATHSEHR ALMSELKILI HIGHHLNVVN 910        920        930        940        950        960
LLGACTKPGG PLMVIVEFCK FGNLSTYLRS KRNEFVPYKT KGARFRQGKD YVGAIPVDLK 970        980        990       1000       1010       1020
RRLDSITSSQ SSASSGFVEE KSLSDVEEEE APEDLYKDFL TLEHLICYSF QVAKGMEFLA 1030       1040       1050       1060       1070       1080
SRKCIHRDLA ARNILLSEKN VVKICDFGLA RDIYKDPDYV RKGDARLPLK WMAPETIFDR 1090       1100       1110       1120       1130       1140
VYTIQSDVWS FGVLLWEIFS LGASPYPGVK IDEEFCRRLK EGTRMRAPDY TTPEMYQTML 1150       1160       1170       1180       1190       1200
DCWHGEPSQR PTFSELVEHL GNLLQANAQQ DGKDYIVLPI SETLSMEEDS GLSLPTSPVS 1210       1220       1230       1240       1250       1260
CMEEEEVCDP KFHYDNTAGI SQYLQNSKRK SRPVSVKTFE DIPLEEPEVK VIPDDNQTDS 1270       1280       1290       1300       1310       1320
GMVLASEELK TLEDRTKLSP SFGGMVPSKS RESVASEGSN QTSGYQSGYH SDDTDTTVYS 1330       1340       1350
SEEAELLKLI EIGVQTGSTA QILQPDSGTT LSSPPV
```

DNA VACCINE FOR USE IN PANCREATIC CANCER PATIENTS

CROSS-REFERENCE TO RELATED APPLICATIONS

This application is a continuation of U.S. application Ser. No. 15/158,387, filed May 18, 2016, which is a continuation of U.S. application Ser. No. 14/409,434, filed Dec. 18, 2014, now U.S. Pat. No. 9,415,098, which is a national stage application under 35 U.S.C. § 371 of International Application No. PCT/EP2013/001882, filed Jun. 26, 2013, which in turn claims priority to European Application No. 12004995.2, filed Jul. 5, 2012, the content of each of which is incorporated herein by reference in its entirety.

SEQUENCE LISTING

The instant application contains a Sequence Listing which has been submitted electronically in ASCII format and is hereby incorporated by reference in its entirety. Said ASCII copy, created on Aug. 22, 2018, is named 108291-0162_SL.txt and is 27,581 bytes in size.

FIELD OF THE INVENTION

The present invention relates to an attenuated mutant strain of *Salmonella* comprising a recombinant DNA molecule encoding a VEGF receptor protein. In particular, the present invention relates to the use of said attenuated mutant strain of *Salmonella* in cancer immunotherapy.

BACKGROUND OF THE INVENTION

Attenuated derivatives of *Salmonella enterica* are attractive vehicles for the delivery of heterologous antigens, such as tumor antigens or tumor stroma antigens, to the mammalian immune system. *S. enterica* strains can potentially be delivered via mucosal routes of immunization, i.e. orally or nasally, which offers advantages of simplicity and safety compared to parenteral administration. Furthermore, *Salmonella* strains elicit strong humoral and cellular immune responses at the level of both systemic and mucosal compartments. Batch preparation costs are relatively low and formulations of live bacterial vaccines are highly stable. Attenuation can be accomplished by deletion of various genes, including virulence, regulatory and metabolic genes.

Several *Salmonella typhimurium* strains attenuated by aro mutations have been shown to be safe and effective delivery vehicles for heterologous antigens in animal models.

Approaches of delivering DNA constructs encoding antigens, in particular VEGF receptor proteins, via live attenuated *Salmonella typhimurium* strains into mouse target cells are described in WO 03/073995. Niethammer et al. (Nature Medicine 2002, 8(12), 1369) describes an attenuated *S. typhimurium* aroA strain SL7207 harboring an expression vector encoding the murine vascular endothelial growth factor receptor 2 (VEGFR-2 or FLK-1) and its use as cancer vaccine.

There is however only one attenuated *Salmonella enterica* serovar strain, namely *Salmonella enterica* serovar *typhi* Ty21a (short: *S. typhi* Ty21a), which has been accepted for use in humans.

This well-tolerated, live oral vaccine against typhoid fever was derived by chemical mutagenesis of the wild-type virulent bacterial isolate *S. typhi* Ty2 and harbors a loss-of-function mutation in the galE gene, as well as other less defined mutations. It has been licensed as typhoid vaccine in many countries after it was shown to be efficacious and safe in field trials.

Angiogenesis contributes to solid tumor growth and metastasis. Compounds like bevacizumab and others, for example small molecules such as sunitinib and axitinib that specifically target the tumor neovasculature have shown efficacy in a range of tumor indications (Powles et al., Br J Cancer 2011, 104(5):741-5); Rini et al., Lancet 2011, 378: 1931-1939).

Tumor neovasculature is lined with endothelial cells that overexpress vascular endothelial growth factor receptor (VEGFR) 2 and are readily accessible via the blood stream. The genetic stability of these cells and their ability to support hundreds of tumor cells per endothelial cell make them a prime target for anti-cancer therapy, be it via antibodies, tyrosine kinase inhibitors, or vaccines (Augustin, Trends Pharmacol Sci 1998, 19:216-222). Recently, T-cell based immunotherapy has gained some clinical success in prostate cancer and validated the potential of anti-cancer vaccination which was often demonstrated pre-clinically (Sharma et al., Nat Rev Cancer 2011, 11:805-812). Activating the immune system against cancer cells faces multiple challenges. For example, cancerous lesions are often polyclonal and cancer cells have the propensity to mutate. Antigen specific therapy often only results in a selection of non-antigen bearing cells. Further hurdles include tumor encapsulation and loss or down-regulation of MHC molecules. Vaccination approaches that target the tumor neovasculature should in theory overcome those hurdles.

OBJECTS OF THE INVENTION

In view of the prior art, it is an object of the present invention to provide a novel safe oral VEGF receptor targeting cancer vaccine. Such a VEGF receptor targeting cancer vaccine would offer major advantages for improving the treatment options for cancer patients.

SUMMARY OF THE INVENTION

The present invention combines anti-angiogenic therapy and vaccination, targeting VEGFR-2 using a new vaccine (VXM01), which is an attenuated and reengineered bacterial strain *Salmonella typhi* Ty21a comprising a plasmid that encodes the VEGF receptor protein 2.

VXM01 represents a novel strategy by targeting not a tumor cell-resident antigen, but a tumor stroma-resident antigen, overexpressed by non-malignant endothelial cells of the tumor neovasculature.

By targeting genetically stable and easily accessible endothelial cells, this product aims to overcome limitations encountered previously by vaccines targeting tumor cells directly, such as tumor-cell heterogeneity, MHC-loss, immunosuppression on a cellular level and tumor encapsulation as well as physiological barriers such as the blood brain barrier. Furthermore, since the therapeutic target is independent of the tumor type, the vaccine may potentially be active against a variety of different solid malignancies. The product represents a patient-independent, "off-the-shelf" oral vaccine, which can be stored and distributed to the clinical sites for use. While anti-angiogenic therapy, either via small molecules or via antibodies, has already been proven to be effective, the approach according to the present invention differs significantly by activating the patient's own immune system against the tumor neovasculature and is as such potentially creating a T-cell memory effect that provides long-term efficacy. Studies with bevacizumab in colon and ovarian cancer suggest that continued anti-angiogenic pressure is required to maintain beneficial treatment effects in the long term (Allegra et al., J Clin Oncol 2011, 29:11-16; Burger et al., N Engl J Med 2011, 365:2473-2483; Perren et al., N Engl J Med 2011, 365:2484-2496).

To the inventors' knowledge, this is the first clinical trial of an oral cancer vaccine. In addition, this vaccine has the potential to be effective against multiple tumor types.

It has been shown by this first clinical trial that the vaccine according to this invention (VXM01) is highly effective in eliciting an immune response that influences significantly the tumor growth in the patient. It is remarkable and surprising that this immune response can be triggered by very low doses of orally administered VXM01. The vaccine is effective at doses starting already with $1\times10^5$ or $1\times10^6$ to $1\times10^7$ colony forming units (CFU). First results indicate that vaccination with VXM01 may lead to the breakdown of existing tumor vasculature and may support the development of an immune memory against proliferating endothelial cells.

The vaccine is effective in monotherapy as well as in a combination therapy with standard chemotherapeutic agents, radiotherapy and/or biological cancer therapy.

In the current clinical trial the stage IV patients were treated in advance and/or simultaneously with the chemotherapeutic agent gemcitabine and VXM01. The treatment with VXM01 is however also effective, if the patients have developed a resistance to chemotherapy (chemo-refractory patients).

In one aspect, the present invention relates to an attenuated mutant strain of *Salmonella typhi* comprising at least one copy of a recombinant DNA molecule comprising an expression cassette encoding a VEGF receptor protein for use as a vaccine.

In particular embodiments, the VEGF receptor protein is selected from the group consisting of human VEGFR-2 and a homolog thereof that shares at least about 80% homology therewith.

In particular embodiments, the VEGF receptor protein is human VEGFR-2 having the amino acid sequence as found in SEQ ID NO 1.

In another aspect, the present invention relates to a DNA vaccine comprising the attenuated mutant strain of *Salmonella typhi* of the present invention.

In particular embodiments, the attenuated mutant strain of *Salmonella typhi* is *Salmonella typhi* Ty21a.

In particular embodiments, the expression cassette is a eukaryotic expression cassette.

In particular embodiments, the DNA vaccine of the present invention is for use in cancer immunotherapy.

In particular embodiments, the DNA vaccine comprises the attenuated *Salmonella typhi* strain Ty21a transformed by a plasmid that contains a DNA encoding the VEGFR-2 protein of SEQ ID NO 1.

In particular embodiments, the DNA vaccine is for use in an anti-angiogenic cancer immunotherapy.

In particular embodiments, the plasmid is the 7580 bp pVAX10.VR2-1 as depicted in FIG. 2 and has the sequence as found in SEQ ID NO 3 and the DNA vaccine is designated VXM01.

In particular embodiments, the cancer is pancreatic cancer.

In particular embodiments, said pancreatic cancer is stage IV or locally advanced pancreatic cancer.

In particular embodiments, the cancer includes metastases.

In particular embodiments, the treatment is accompanied by chemotherapy and/or radiotherapy.

In particular embodiments, the chemotherapeutic agent is gemcitabine.

In particular embodiments, the immunotherapeutic treatment with the vaccine is carried out during the chemotherapy treatment cycle.

In particular embodiments, the vaccine is administered orally.

In particular embodiments, the single dose of the vaccine is $1\times10^5$, $1\times10^6$, $1\times10^7$, $1\times10^8$, $1\times10^9$, $1\times10^{10}$, or $1\times10^{11}$ colony forming units (CFU).

In particular embodiments, the single dose of the vaccine is less than $1\times10^9$ CFU. In particular embodiments, the single dose of the vaccine is from $1\times10^8$ to $1\times10^9$ CFU.

In particular embodiments, the single dose of the vaccine is less than $1\times10^8$ CFU. In particular embodiments, the single dose of the vaccine is from $1\times10^5$ to $1\times10^8$ CFU, more particularly the single dose of the vaccine is from $1\times10^6$ to $1\times10^7$ CFU.

In particular embodiments, the single dose comprises from about $10^5$ to about $10^{11}$, particularly form about $10^6$ to about $10^{10}$, more particularly from about $10^6$ to about $10^9$, more particularly from about $10^6$ to about $10^8$, most particularly from about $10^6$ to about $10^7$ colony forming units (CFU).

In another aspect, the present invention relates to the DNA vaccine VXM01, comprising the attenuated *Salmonella typhi* strain Ty21a transformed by a plasmid that contains a DNA encoding the VEGFR-2 protein of SEQ ID NO 1, wherein the plasmid is a 7580 bp plasmid DNA and comprises the cDNA of VEGFR-2 that is under the control of the CMV promoter, the kanamycin resistance gene, and the pMB1 ori, and is designated as pVAX10.VR2-1.

DETAILED DESCRIPTION OF THE INVENTION

The present invention may be understood more readily by reference to the following detailed description of the invention and the examples included therein.

In one aspect, the present invention relates to an attenuated mutant strain of *Salmonella typhi* comprising at least one copy of a recombinant DNA molecule comprising an expression cassette encoding a VEGF receptor protein.

According to the invention, the attenuated mutant strain of *Salmonella typhi* functions as the bacterial carrier of the recombinant DNA molecule comprising an expression cassette encoding a VEGF receptor protein for the delivery of said recombinant DNA molecule into a target cell.

In the context of the present invention, the term "attenuated" refers to a bacterial strain of reduced virulence compared to the parental bacterial strain, not harboring the attenuating mutation. Attenuated bacterial strains have preferably lost their virulence but retained their ability to induce protective immunity. Attenuation can be accomplished by deletion of various genes, including virulence, regulatory, and metabolic genes. Attenuated bacteria may be found naturally or they may be produced artificially in the laboratory, for example by adaptation to a new medium or cell culture or they may be produced by recombinant DNA technology.

In the context of the present invention, the term "mutant strain" refers to a bacterial strain harboring a mutation in its genome. In this context, the term "mutation" refers to a change in the nucleic acid sequence, including point mutations, insertions, deletions, translocations and inversions.

In the context of the present invention, the term "comprises" or "comprising" means "including, but not limited to". The term is intended to be open-ended, to specify the presence of any stated features, elements, integers, steps or components, but not to preclude the presence or addition of one or more other features, elements, integers, steps, components or groups thereof. The term "comprising" thus includes the more restrictive terms "consisting of" and "essentially consisting of". In one embodiment the term "comprising" as used throughout the application and in particular within the claims may be replaced by the term "consisting of".

In the context of the present invention, the term "recombinant DNA molecule" refers to an engineered DNA construct, preferably composed of DNA pieces of different origin. The recombinant DNA molecule can be a linear nucleic acid, or preferably, a circular recombinant DNA plasmid generated by introducing an open reading frame encoding a VEGF receptor protein into an expression vector plasmid.

In the context of the present invention, the term "expression cassette" refers to a nucleic acid unit comprising at least a VEGF receptor protein under the control of regulatory sequences controlling its expression. The expression cassette comprised in the attenuated mutant strain of Salmonella can preferably mediate transcription of the included open reading frame encoding a VEGF receptor protein in a target cell. Expression cassettes typically comprise a promoter, at least one open reading frame and a transcription termination signal.

VEGF receptor proteins are endothelial cell-specific receptor-tyrosine kinases that can be bound by the ligand vascular endothelial growth factor (VEGF) which causes them to dimerize and become activated through transphosphorylation. The VEGF family of growth factors (Kd 75-760 pM) encompasses 6 family members, VEGF-A (also known as VEGF) through E and PLGF (placental growth factor, also known as PGF or PlGF-2). VEGF growth factors regulate growth and differentiation of multiple components of the vascular system, especially blood and lymph vessels. There are three main subtypes of VEGFR, VEGFR-1 (or FLT1), VEGFR-2 (or KDR, FLK1) and VEGFR-3 (or FLT4). Membrane-bound VEGF receptors have an extracellular portion consisting of 7 immunoglobulin-like domains, a single transmembrane spanning region and an intracellular portion containing a split tyrosine-kinase domain. VEGFR transcripts give also rise to alternative splice variants that encode soluble VEGF receptor proteins.

VEGFR-2, also known as kinase-insert-domain-containing receptor (KDR), appears to mediate almost all of the known cellular responses to VEGF. For example, the role of VEGF in angiogenesis appears to be mediated through the interaction of this protein with VEGFR-2. VEGFR-2 is a 1356 amino acid long, 200-230 kDa molecular weight high-affinity receptor for VEGF, as well as for VEGF-C and VEGF-D. Identified in humans through the screening of endothelial cDNA for tyrosine kinase receptors, VEGFR-2 shares 85% sequence identity with the previously discovered mouse fetal liver kinase 1 (Flk-1). VEGFR-2 is normally expressed in endothelial and hematopoietic precursors, as well as in endothelial cells, nascent hematopoietic stem cells and the umbilical cord stroma. However, in quiescent adult vasculature, VEGFR-2 mRNA appears to be down regulated.

The extracellular domain of VEGFR-2 contains 18 potential N-linked glycosylation sites. VEGFR-2 is initially synthesized as a 150 kDa protein and rapidly glycosylated to a 200 kDa intermediate form, and then further glycosylated at a slower rate to a mature 230 kDa protein which is expressed on the cell surface.

The amino acid sequence of the human VEGFR-2 encoding cDNA sequence cloned into the pVAX10.VR2-1 plasmid is presented in FIG. 1.

In particular embodiments, the attenuated mutant strain of Salmonella typhi of the present invention is for use as a medicament.

In particular embodiments, the attenuated mutant strain of Salmonella typhi of the present invention is for use as a vaccine.

In the context of the present invention, the term "vaccine" refers to an agent which is able to induce an immune response in a subject upon administration. A vaccine can preferably prevent, ameliorate or treat a disease. A vaccine in accordance with the present invention comprises an attenuated mutant strain of Salmonella typhi, preferably S. typhi Ty21a. The vaccine in accordance with the present invention further comprises at least one copy of a recombinant DNA molecule comprising an expression cassette, preferably a eukaryotic expression cassette, encoding a VEGF receptor protein, preferably selected from human VEGFR-2 or a protein that shares at least about 80% sequence identity therewith.

The live attenuated Salmonella mutant strain according to the present invention comprising a recombinant DNA molecule encoding a VEGF receptor protein can be used as a vehicle for the oral delivery of this recombinant DNA molecule. Such a delivery vector comprising a DNA molecule encoding a heterologous antigen, such as a VEGF receptor protein, is termed DNA vaccine.

Genetic immunization might be advantageous over conventional vaccination. The target DNA can be detected for a considerable period of time thus acting as a depot of the antigen. Sequence motifs in some plasmids, like GpC islands, are immunostimulatory and can function as adjuvants furthered by the immunostimulation due to LPS and other bacterial components. Live bacterial vectors produce their own immunomodulatory factors such as lipopolysaccharides (LPS) in situ which may constitute an advantage over other forms of administration such as microencapsulation. Moreover, the use of the natural route of entry proves to be of benefit since many bacteria, like Salmonella, egress from the gut lumen via the M cells of Peyer's patches and migrate eventually into the lymph nodes and spleen, thus allowing targeting of vaccines to inductive sites of the immune system.

Furthermore, attenuated derivatives of Salmonella enterica are attractive as vehicles for the delivery of heterologous antigens the mammalian immune system, because S. enterica strains can potentially be delivered via mucosal routes of immunization, i.e. orally or nasally, which offers advantages of simplicity and safety compared to parenteral administration. Furthermore, Salmonella strains elicit strong humoral and cellular immune responses at the level of both systemic and mucosal compartments.

In particular embodiments, the attenuated mutant strain of Salmonella typhi is Salmonella typhi Ty21a. The vaccine strain Ty21a has been demonstrated to date to have an excellent safety profile. Upon exit from the gut lumen via the M cells, the bacteria are taken up by phagocytic cells, such as macrophages and dendritic cells. These cells are activated by the pathogen and start to differentiate, and probably migrate, into the lymph nodes and spleen. Due to the attenuating mutations, bacteria of the S. typhi Ty21a strain are not able to persist in these phagocytic cells but die at this time point. The recombinant DNA molecules are released and subsequently transferred into the cytosol of the phagocytic immune cells, either via a specific transport system or by endosomal leakage. Finally, the recombinant DNA molecules enter the nucleus, where they are transcribed, leading to VEGF receptor expression in the cytosol of the phagocytic cells. Specific cytotoxic T cells against the VEGFR receptor protein are induced by the activated antigen presenting cells (APCs).

There is no data available to-date indicating that *S. typhi* Ty21a is able to enter the bloodstream systemically. The live attenuated *Salmonella typhi* Ty21a vaccine strain thus allows specific targeting of the immune system while exhibiting an excellent safety profile.

In particular embodiments, the VEGF receptor protein is selected from the group consisting of human VEGFR-2 and a homolog thereof that shares at least about 80% homology therewith.

In this context, the term "about" or "approximately" means within 80% to 120%, alternatively within 90% to 110%, including within 95% to 105% of a given value or range.

In the context of the present invention, the term "protein that has at least about 80% sequence identity with human VEGFR-2" refers to a protein that differs in the amino acid sequence and/or the nucleic acid sequence encoding the amino acid sequence of human VEGFR-2. The protein may be of natural origin, e.g. a homolog of VEGFR-2 of a different species, or an engineered protein, e.g. an engineered VEGFR-2 derivative. It is known that the usage of codons is different between species. Thus, when expressing a heterologous protein in a target cell, it may be necessary, or at least helpful, to adapt the nucleic acid sequence to the codon usage of the target cell. Methods for defining and constructing derivatives of a given protein are well-known to any one of ordinary skill in the art.

The protein that shares at least about 80% sequence identity with human VEGFR-2 may contain one or more mutations comprising an addition, a deletion and/or a substitution of one or more amino acids. According to the teaching of the present invention, said deleted, added and/or substituted amino acids may be consecutive amino acids or may be interspersed over the length of the amino acid sequence of the protein that shares at least about 80% sequence identity with human VEGFR-2. According to the teaching of the present invention, a number of amino acids may be added, deleted, and/or substituted, as long as the sequence identity with human VEGFR-2 is at least about 80%. In particular embodiments, the sequence identity with human VEGFR-2 is at least about 80%, at least about 85%, at least about 90%, or most particularly at least about 95%. Methods and algorithms for determining sequence identity including the comparison of the parental protein and its derivatives having deletions, additions and/or substitutions relative to a parental sequence, are well-known to the practitioner of ordinary skill in the art. On the DNA level, the nucleic acid sequences encoding the protein that has at least about 80% sequence identity with human VEGFR-2 may differ to a larger extent due to the degeneracy of the genetic code.

In particular embodiments, the VEGF receptor protein is human VEGFR-2 having the amino acid sequence as found in SEQ ID NO 1.

In another aspect, the present invention relates to a DNA vaccine comprising the attenuated mutant strain of *Salmonella typhi* of the present invention.

In particular embodiments, the attenuated mutant strain of *Salmonella typhi* is *Salmonella typhi* Ty21a. The attenuated *S. typhi* Ty21a strain is an active component of Typhoral L®, also known as Vivotif® (manufactured by Berna Biotech Ltd., a Crucell Company, Switzerland). It is currently the only licensed live oral vaccine against typhoid fever. This vaccine has been extensively tested and has proved to be safe regarding patient toxicity as well as transmission to third parties (Wandan et al., J. Infectious Diseases 1982, 145:292-295). The vaccine is licensed in more than 40 countries. The Marketing Authorization number of Typhoral L® is PL 15747/0001 dated 16 Dec. 1996. One dose of vaccine contains at least $2\times10^9$ viable *S. typhi* Ty21a colony forming units and at least $5\times10^9$ non-viable *S. typhi* Ty21a cells.

One of the biochemical properties of the *Salmonella typhi* Ty21a bacterial strain is its inability to metabolize galactose. The attenuated mutant strain is also not able to reduce sulfate to sulfite which differentiates it from the wild type *Salmonella* Ty2 strain. With regard to its serological characteristics, the *Salmonella typhi* Ty21a strain contains the 09-antigen which is a polysaccharide of the outer membrane of the bacteria and lacks the 05-antigen which is in turn a characteristic component of *Salmonella typhimurium*. This serological characteristic supports the rationale for including the respective test in a panel of identity tests for batch release.

In particular embodiments, the expression cassette is a eukaryotic expression cassette. In the context of the present invention, the term "eukaryotic expression cassette" refers to an expression cassette which allows for expression of the open reading frame in a eukaryotic cell. It has been shown that the amount of heterologous antigen required to induce an adequate immune response may be toxic for the bacterium and result in cell death, over-attenuation or loss of expression of the heterologous antigen. Using a eukaryotic expression cassette that is not expressed in the bacterial vector but only in the target cell may overcome this toxicity problem and the protein expressed may exhibit a eukaryotic glycosylation pattern.

A eukaryotic expression cassette comprises regulatory sequences that are able to control the expression of an open reading frame in a eukaryotic cell, preferably a promoter and polyadenylation signal. Promoters and polyadenylation signals included in the recombinant DNA molecules comprised by the attenuated mutant strain of *Salmonella* of the present invention are preferably selected to be functional within the cells of the subject to be immunized. Examples of suitable promoters, especially for the production of a DNA vaccine for humans, include but are not limited to promoters from cytomegalovirus (CMV), such as the strong CMV immediate early promoter, Simian virus 40 (SV40), Mouse Mammary Tumor Virus (MMTV), Human Immunodeficiency Virus (HIV), such as the HIF Long Terminal Repeat (LTR) promoter, Moloney virus, Epstein Barr Virus (EBV), and from Rous Sarcoma Virus (RSV) as well as promoters from human genes such as human actin, human myosin, human hemoglobin, human muscle creatine, and human metallothionein. In a particular embodiment, the eukaryotic expression cassette contains the CMV promoter. In the context of the present invention, the term "CMV promoter" refers to the strong immediate-early cytomegalovirus promoter.

Examples of suitable polyadenylation signals, especially for the production of a DNA vaccine for humans, include but are not limited to the bovine growth hormone (BGH) polyadenylation site, SV40 polyadenylation signals and LTR polyadenylation signals. In a particular embodiment, the eukaryotic expression cassette included in the recombinant DNA molecules comprised by the attenuated mutant strain of *Salmonella* of the present invention comprises the BGH polyadenylation site.

In addition to the regulatory elements required for expression of the VEGF receptor protein, like a promoter and the polyadenylation signal, other elements can also be included in the recombinant DNA molecule. Such additional elements include enhancers. The enhancer can be, for example, the enhancer of human actin, human myosin, human hemoglobin, human muscle creatine and viral enhancers such as those from CMV, RSV and EBV.

Regulatory sequences and codons are generally species dependent, so in order to maximize protein production, the regulatory sequences and codons are preferably selected to be effective in the species to be immunized. The person skilled in the art can produce recombinant DNA molecules that are functional in a given subject species.

In particular embodiments, the DNA vaccine of the present invention is for use in cancer immunotherapy.

In particular embodiments, the DNA vaccine comprises the attenuated *Salmonella typhi* strain Ty21a transformed by a plasmid that contains a DNA encoding the VEGFR-2 protein of SEQ ID NO 1.

In particular embodiments, the DNA vaccine is for use in an anti-angiogenic cancer immunotherapy.

In particular embodiments, the recombinant DNA molecule comprises the kanamycin antibiotic resistance gene, the pMB1 ori, and a eukaryotic expression cassette encoding human VEGFR-2 or a protein that shares at least 80% sequence homology therewith, under the control of a CMV promoter. In particular embodiments, human VEGFR-2 has the nucleic acid sequence as found in SEQ ID NO 2.

The eukaryotic Cytomegalovirus (CMV) immediate-early promoter ensures efficient translation of the VEGFR-2 protein in the host cell, and the prokaryotic origin of replication (ori) mediates multiplication within the bacterial host.

In particular embodiments, the recombinant DNA molecule is derived from commercially available pVAX1™ expression plasmid (Invitrogen, San Diego, Calif.). This expression vector was modified by replacing the high copy pUC origin of replication by the low copy pMB1 origin of replication of pBR322. The low copy modification was made in order to reduce the metabolic burden and to make the construct more stable. Details of the plasmid pVAX10.VR2-1 construct are depicted in FIG. 2. The generated expression vector backbone was designated pVAX10. Inserting human VEGFR-2 of the nucleic acid sequence as found in SEQ ID NO 2 into this expression vector backbone yielded the expression plasmid pVAX10.VR2-1.

The expression plasmid pVAX10.VR2-1 is schematically depicted in FIG. 2. In particular embodiments, the plasmid is the 7580 bp pVAX10.VR2-1 as depicted in FIG. 2 and has the sequence as found in SEQ ID NO 3 and the DNA vaccine is designated VXM01. VXM01 is an oral cancer vaccine consisting of an attenuated strain of *Salmonella enterica* serovar *typhi* Ty21a carrying at least one copy of a plasmid DNA, pVAX10.VR2-1, encoding a eukaryotic expression cassette of the human Vascular Endothelial Growth Factor-Receptor 2 (VEGFR-2).

In particular embodiments, the cancer is pancreatic cancer.

In particular embodiments, said pancreatic cancer is stage IV or locally advanced pancreatic cancer.

In particular embodiments, the cancer includes metastases.

In particular embodiments, cancer immunotherapy further comprises administration of one or more further attenuated mutant strain(s) of *Salmonella* comprising at least one copy of a recombinant DNA molecule comprising an expression cassette encoding a tumor antigen and/or a tumor stroma antigen. In particular embodiments, said one or more further mutant strain(s) of *Salmonella* is/are *Salmonella typhi* Ty21a comprising a eukaryotic expression cassette. In particular embodiments, said one or more further strain(s) of *Salmonella* comprise(s) an attenuated mutant strain of *Salmonella* encoding human WT1.

Combining the attenuated mutant strain of *Salmonella* of the present invention with a second attenuated mutant strain comprising a DNA molecule encoding a second tumor stroma antigen or a tumor antigen may have synergistic antitumor effects. In particular, simultaneous targeting of the tumor and the tumor stroma may minimize the risk of tumor escape. Combining VEGFR-2 based immunotherapy with WT1 based cancer immunotherapy may prove especially effective, since WT1 overexpressing human cells and the tumor vasculature are attacked at the same time.

In particular embodiments, the attenuated mutant strain of *Salmonella* is co-administered with said one or more further attenuated mutant strain(s) of *Salmonella*.

In the context of the present invention, the term "co-administration" or "co-administer" means administration of two different attenuated mutant strains of *Salmonella* within three consecutive days, more particularly within two consecutive days, more particularly on the same day, more particularly within 12 hours. Most particularly, in the context of the present invention, the term "co-administration" refers to simultaneous administration of two different attenuated mutant strains of *Salmonella*.

In particular embodiments, the treatment is accompanied by chemotherapy and/or radiotherapy and/or biological cancer therapy. For cure of cancer, complete eradication of cancer stem cells may be essential. For maximal efficacy, a combination of different therapy approaches may be beneficial.

In the context of the present invention, the term "biological cancer therapy" or "cancer immunotherapy" refers to the stimulation of the patient's immune system to attack malignant tumor cells or the tumor stroma. Biological cancer therapy approaches include delivery of tumor antigens, delivery of therapeutic antibodies as drugs, administration of immunostimulatory cytokines and administration of immune cells.

Chemotherapeutic agents that may be used in combination with the attenuated mutant strain of *Salmonella* of the present invention may be, for example: amifostine (ethyol), cabazitaxel, cisplatin, dacarbazine (DTIC), dactinomycin, docetaxel, mechlorethamine, streptozocin, cyclophosphamide, carrnustine (BCNU), lomustine (CCNU), doxorubicin (adriamycin), doxorubicin lipo (doxil), folinic acid, gemcitabine (gemzar), daunorubicin, daunorubicin lipo (daunoxome), procarbazine, ketokonazole, mitomycin, cytarabine, etoposide, methotrexate, 5-fluorouracil (5-FU), vinblastine, vincristine, bleomycin, paclitaxel (taxol), docetaxel (taxotere), aldesleukin, asparaginase, busulfan, carboplatin, cladribine, camptothecin, CPT-11, 10-hydroxy-7-ethyl-camptothecin (SN38), dacarbazine, floxuridine, fludarabine, hydroxyurea, ifosfamide, idarubicin, mesna, interferon alpha, interferon beta, irinotecan, mitoxantrone, topotecan, leuprolide, megestrol, melphalan, mercaptopurine, oxaliplatin, plicamycin, mitotane, pegaspargase, pentostatin, pipobroman, plicamycin, streptozocin, tamoxifen, teniposide, testolactone, thioguanine, thiotepa, uracil mustard, vinorelbine, chlorambucil and combinations thereof.

Most preferred chemotherapeutic agents according to the invention in combination with VXM01 are cabazitaxel, carboplatin, oxaliplatin, cisplatin, cyclophosphamide, docetaxel, gemcitabine, doxorubicin, paclitaxel (taxol), irinotecan, vincristine, vinblastine, vinorelbin, folinic acid, 5-fluorouracil and bleomycin, especially gemcitabine.

In particular embodiments, the chemotherapeutic agent is gemcitabine.

It may be also favorable dependent on the occurrence of possible side effects to include treatment with antibiotics or anti-inflammatory agents.

Should adverse events occur that resemble hypersensitivity reactions mediated by histamine, leukotrienes, or cytokines, treatment options for fever, anaphylaxis, blood pressure instability, bronchospasm, and dyspnoea are available. Treatment options in case of unwanted T-cell derived auto-aggression are derived from standard treatment schemes in acute and chronic graft vs. host disease applied after stem cell transplantation. Cyclosporin and glucocorticoids are proposed as treatment options.

In the unlikely case of systemic *Salmonella typhi* Ty21a type infection, appropriate antibiotic therapy is recommended, for example with fluoroquinolones including ciprofloxacin or ofloxacin. Bacterial infections of the gastrointestinal tract are to be treated with respective agents, such as rifaximin.

In particular embodiments, the attenuated mutant strain of *Salmonella* is administered during the chemotherapy or the radiotherapy treatment cycle or during biological cancer therapy. In particular embodiments, the immunotherapeutic treatment with the vaccine is carried out during the chemotherapy treatment cycle.

In particular embodiments, the attenuated mutant strain of *Salmonella* is administered before the chemotherapy or the radiotherapy treatment cycle or before biological cancer therapy. This approach may have the advantage that chemotherapy or radiotherapy can be performed under conditions of enhanced cancer immunity.

In particular embodiments, the attenuated mutant strain of *Salmonella* is administered after the chemotherapy or the radiotherapy treatment cycle or after biological cancer therapy.

In particular embodiments, the vaccine is administered orally. Oral administration is simpler, safer and more comfortable than parenteral administration. Adverse effects of parenteral, subcutaneous or intradermal administration may be overcome by oral administration of the DNA vaccine of the present invention. The attenuated mutant strain of *Salmonella* of the present invention may however also be administered by any other suitable route. Preferably, a therapeutically effective dose is administered to the subject, and this dose depends on the particular application, the type of malignancy, the subject's weight, age, sex and state of health, the manner of administration and the formulation, etc. Administration may be single or multiple, as required.

The attenuated mutant strain of *Salmonella* of the present invention may be provided in the form of a solution, a suspension, lyophilisate, or any other suitable form. It may be provided in combination with pharmaceutically acceptable carriers, diluents, and/or excipients. Agents for adjusting the pH value, buffers, agents for adjusting toxicity, and the like may also be included. In the context of the present invention, the term "pharmaceutically acceptable" refers to molecular entities and other ingredients of pharmaceutical compositions that are physiologically tolerable and do not typically produce untoward reactions when administered to a mammal (e.g., human). The term "pharmaceutically acceptable" may also mean approved by a regulatory agency of a Federal or a state government or listed in the U.S. Pharmacopeia or other generally recognized pharmacopeia for use in mammals, and, more particularly, in humans.

The vaccine of the present invention is surprisingly effective at relatively low doses. In particular embodiments, the single dose of the vaccine is about $1\times10^5$, about $1\times10^6$, about $1\times10^7$, about $1\times10^8$, about $1\times10^9$, about $1\times10^{10}$, or about $1\times10^{11}$ colony forming units (CFU). Administration of low doses of this live bacterial vaccine minimizes the risk of excretion and thus of transmission to third parties.

In this context, the term "about" or "approximately" means within a factor of 3, alternatively within a factor of 2, including within a factor of 1.5 of a given value or range.

In particular embodiments, the single dose of the vaccine is less than about $1\times10^9$ CFU. In particular embodiments, the single dose of the vaccine is from $1\times10^8$ to $1\times10^9$ CFU.

In particular embodiments, the single dose of the vaccine is less than about $1\times10^8$ CFU. In particular embodiments, the single dose of the vaccine is from $1\times10^5$ to $1\times10^8$ CFU, more particularly the single dose of the vaccine is from $1\times10^6$ to $1\times10^7$ CFU.

In particular embodiments, the single dose comprises from about $10^5$ to about $10^{11}$, particularly form about $10^6$ to about $10^{10}$, more particularly from about $10^6$ to about $10^9$, more particularly from about $10^6$ to about $10^8$, most particularly from about $10^6$ to about $10^7$ colony forming units (CFU).

In particular embodiments, the attenuated mutant strain of *Salmonella* is for use in individualized cancer immunotherapy. Individualized cancer immunotherapy may comprise the step of assessing the tumor stroma antigen expression pattern and/or the tumor antigen expression pattern of a patient. Individualized cancer immunotherapy may also comprise the step of assessing pre-immune responses against a tumor stroma antigen or a tumor antigen, preferably the pre-immune response against VEGFR-2. In line with this, pre-existing immune responses against VEGFR-2 were shown to strongly correlate with positive clinical responses of VXM01, in particular with a decrease in tumor perfusion.

VXM01 can be used—either by itself or in combination with other *Salmonella typhi* Ty21a based cancer vaccines comprising eukaryotic expression systems—for the treatment of various cancer types. In particular embodiments, VXM01 may be used for individualized patient specific cancer treatment. For that purpose, the patient's stromal and/or tumor antigen expression pattern may be assessed in a first step for example by companion diagnostics targeting the patient's specific stromal and/or tumor antigen pattern. Alternatively, pre-existing immune responses against stromal and/or tumor antigens may be assessed. Depending on the patient's stromal and/or tumor antigen expression pattern, VMX01 may be administered either alone or in combination with one or more suitable further *Salmonella typhi* Ty21a based cancer vaccine(s) comprising eukaryotic expression systems. Combinations of VXM01 with one or more further *Salmonella typhi* Ty21a based cancer vaccine(s) may however also be administered as fixed combinations. These cocktails combining two or more *Salmonella typhi* Ty21a based cancer vaccines can be composed of separate off the shelf products. The combinations, either fixed or individualized, may contain VXM01 as anti-angiogenic basis therapy.

In another aspect, the present invention relates to the DNA vaccine VXM01, comprising the attenuated *Salmonella typhi* strain Ty21a transformed by a plasmid that contains a DNA encoding the VEGFR-2 protein of SEQ ID NO 1, wherein the plasmid is a 7580 bp plasmid DNA and comprises the cDNA of VEGFR-2 that is under the control of the CMV promoter, the kanamycin resistance gene, and the pMB1 ori, and is designated as pVAX10.VR2-1.

SHORT DESCRIPTION OF FIGURES AND TABLES

Figure 6:
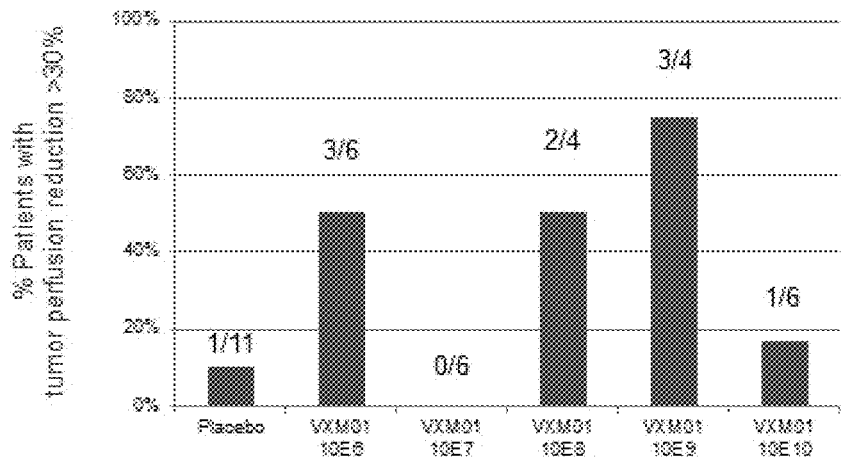
Figure 7:
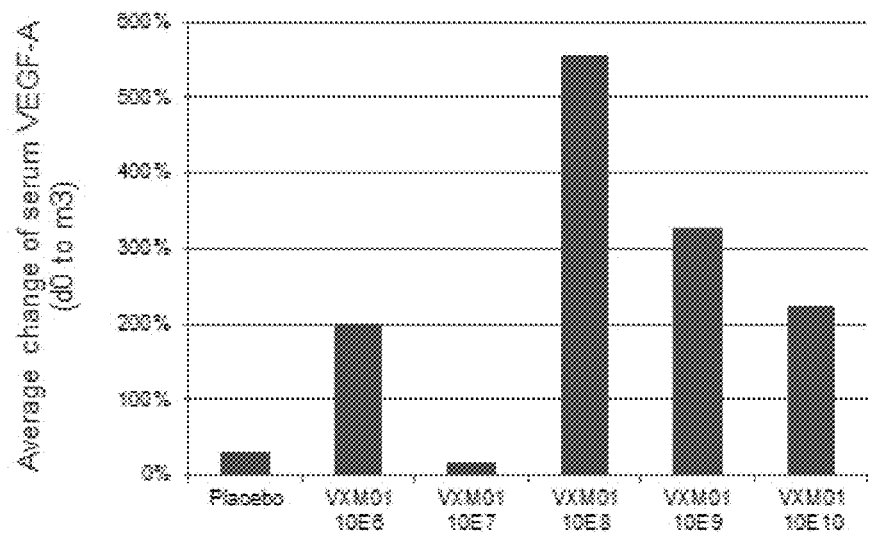
Figure 8:
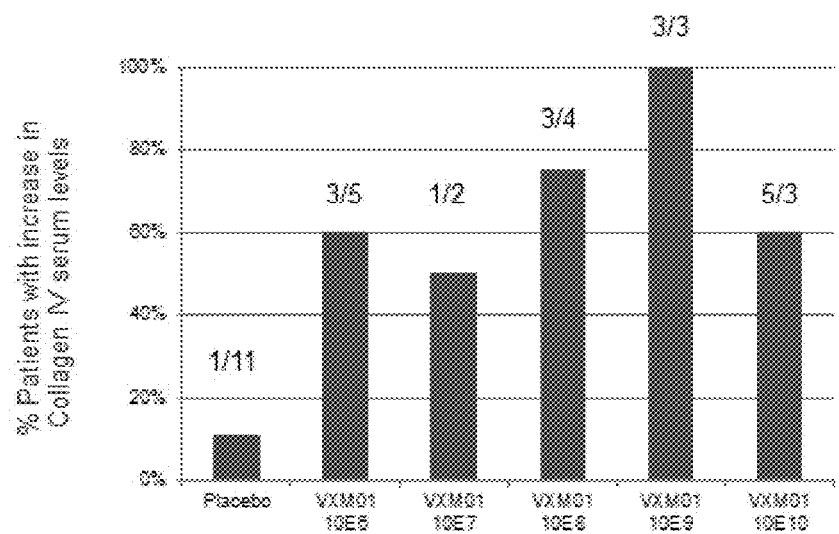
Figure 9:
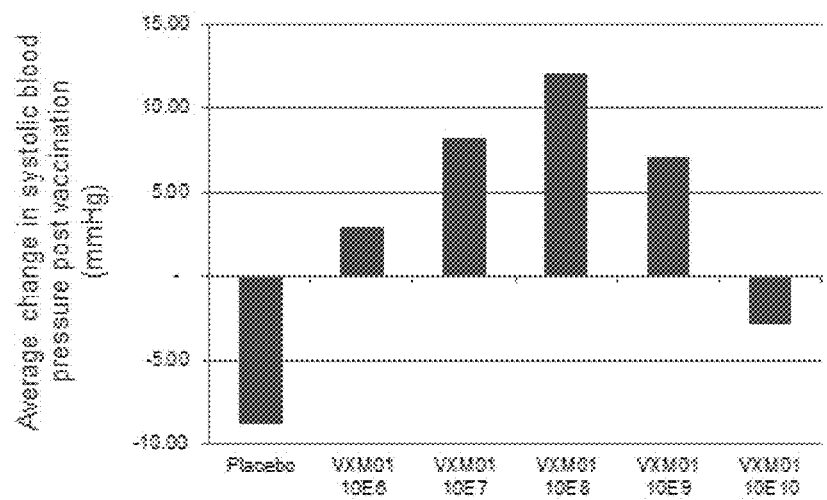
Figure 11:
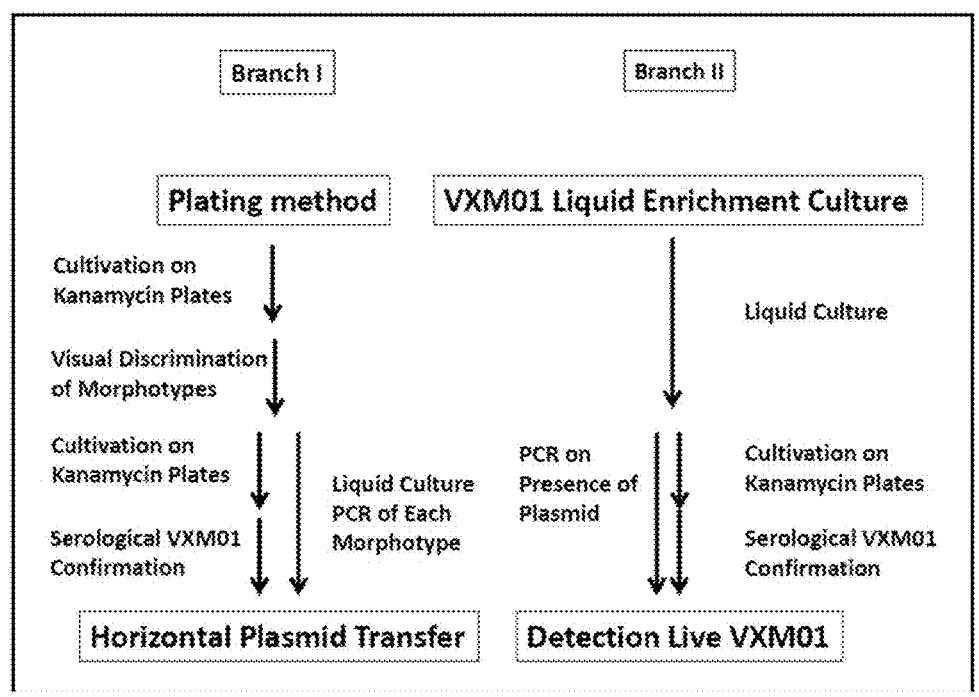
Figure 12:
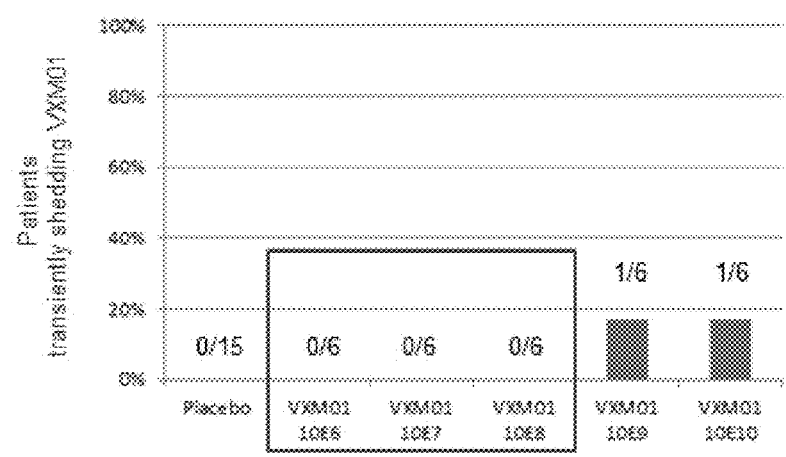

FIG. 1: Amino acid sequence of VEGFR-2 cDNA cloned into plasmid pVAX10.VR2-1
FIG. 2: Plasmid map of pVAX10.VR2-1
FIG. 3: Dose escalating design of vaccine VXM01
FIG. 4: Overall study scheme
FIG. 5: VXM01 specific T cell responses
FIG. 6: Effects of VXM01 on tumor perfusion
FIG. 7: Effects of VXM01 on VEGF A serum levels
FIG. 8: Effects of VXM01 on collagen IV serum levels
FIG. 9: Effects of VXM01 on blood pressure
FIG. 10: VXM01-induced anti-carrier immunity
FIG. 11: Analysis cascade of VXM01 excretion
FIG. 12: VXM01 excretion
Table 1: Patient selection criteria
Table 2: VMX01 specific T cell responses

EXAMPLES

Example 1 *Salmonella typhi* Ty21a Strain Preparation and Plasmid Preparation

The first step in the preparation of the research seed lot (RSL) consisted of the isolation of the attenuated *Salmonella typhi* Ty21a strain followed by the transformation of the attenuated bacteria with the plasmid DNA (pVAX10.VR2-1).

Liquid culture medium was inoculated with a *Salmonella typhi* Ty21a isolate and the liquid culture was then plated onto an agar medium for the purpose of isolating single bacterial colonies. Single colonies were isolated and grown in liquid culture medium. Two cultures, namely VAX.Ty21-1 and VAX.Ty21-2, were then formulated with glycerol, aliquoted (1 ml) and stored at −75° C.±5° C. pending use. Identity of each of the two cultures was further confirmed.

The principle of plasmid synthesis was based on double strand in vitro gene synthesis with the following steps:

- The whole pVAX10-VR2.1 plasmid sequence of 7.58 kb was subdivided (by software analysis) in 5 sections of ~1.5 kb. Each section was subdivided into 40-50 bp oligonucleotides each having overlapping regions between oligonucleotides of both strands
- The in vitro synthesized oligonucleotides were then phosphorylated by incubation with T4 polynucleotide kinase
- After the annealing process of overlapping oligonucleotides under appropriate conditions, the Taq DNA ligase enzyme connected the aligned oligonucleotides
- Upon completion of the ligation step, PCR was performed using primers annealed at outward positions, to increase the yield of the ligated plasmid fragments (~1.5 kb)
- A preparative agarose gel electrophoresis was performed to isolate the PCR products
- The isolated PCR products were cloned into TOPO vectors (Invitrogen K#4575-40) and transformed into TOP10 *E. coli* cells for propagation
- After TOPO plasmid isolation, a restriction and sequence verification was performed
- The isolated aligned fragments were assembled via overlap PCR. This process was followed by linearly assembling the pVAX10.VR2-1 plasmid
- After XhoI restriction digest (single restriction site is present in the pVAX10.VR2-1 plasmid, see FIG. 2) and covalent binding via T4 ligase, *E. coli* was transformed with the circular plasmid for propagation
- After final plasmid sequence verification, the pVAX10.VR2-1 plasmid was transformed into the *S. typhi* Ty21a bacterial strain.

The plasmid pVAX10.VR2-1 was thus successfully synthesized (no deviation to reference sequence). This plasmid was further used to transform the *S. typhi* Ty21a bacterial strain.

Example 2 VXM01—Phase I Clinical Trial; Study Description

This phase I trial examined the safety, tolerability, and immunological and clinical responses to VXM01. The randomized, placebo-controlled, double blind dose-escalation study included 45 patients with locally advanced or stage IV pancreatic cancer. The patients received four doses of VXM01 or placebo in addition to gemcitabine as standard of care. Doses from $10^6$ CFU up to $10^{10}$ CFU of VXM01 were evaluated in the study. An independent data safety monitoring board (DSMB) was involved in the dose-escalation decisions. In addition to safety as primary endpoint, the VXM01-specific immune reaction, as well as clinical response parameters were evaluated.

Preclinical Efficacy Assessment:

The efficacy and safety of this approach in animals has been validated multiple times by the inventors. Further experiments by the inventors showed an activity of this vaccine in two different models of pancreatic cancer.

VXM01, the vaccine used in this trial, is a humanized version of the anti-VEGFR-2 vaccine previously tested in mice. It encodes the human full-length VEGFR-2 and uses the licensed *Salmonella typhi* strain Ty21a instead of *Salmonella typhimurium* as a carrier. The vaccine is assumed to lead to VEGFR-2 protein expression in monocytes and dendritic cells after entry of VXM01 in the Peyer's patches via M cells of the gut, and internalization by antigen-presenting cells followed by translation of the encoded DNA.

Preclinical Safety Assessment:

Preclinical toxicity studies in mice included, but were not restricted to a single dose toxicity study in mice conducted with the human vaccine VXM01. As VXM01 is specific for the human host, the study of the human vaccine in mice focused on possible effects of process-related impurities and related signs and symptoms of possible relevance for cardiovascular, respiratory, or central nervous system impairment. In order to investigate the toxicity profile of an anti-VEGFR-2 T-cell response, a repeated dose toxicity study was conducted using the murine analog construct of VXM01 which induced a dose-dependent T-cell response in mice. In accordance to the inventors' previous observations, no treatment-related deaths and no toxicologically important clinical signs were observed throughout these studies, which were conducted according to Good Laboratory Practice (GLP).

The vector *Salmonella typhi* Ty21a used here is a live, attenuated bacterial carrier that allows for the oral delivery of the vaccine VXM01. It is itself an approved vaccine against typhoid fever (Vivotif®, Crucell, formerly Berna Biotech Ltd., Switzerland) that has been extensively tested and has demonstrated its safety regarding patient toxicity as well as transmission to third parties (Wandan et al., J. Infectious Diseases 1982, 145:292-295). VXM01 is classified as a gene transfer medicinal product and subject to the respective guidance and regulations.

Study Descriptions and Objectives:

The conducted study was a monocenter, placebo controlled, double blind dose escalation study of the experimental vaccine VXM01 in patients with inoperable or stage IV pancreatic cancer. The vaccine was given as add-on to a standard of care gemcitabine treatment.

The objectives were to examine the safety and tolerability, and immunological and clinical responses to the investigational anti-VEGFR-2 vaccine VXM01, as well as to identify the maximum tolerated dose (MTD) of VXM01. The MTD is defined as the highest dose level at which less than two of up to six patients under VXM01 treatment experience a dose-limiting toxicity (DLT).

Primary endpoints for safety and tolerability were as follows: Number of DLTs defined as any adverse event (AE) related to study drug of grade 4 or higher, or grade 3 or higher for gastrointestinal fistula, diarrhea, gastrointestinal perforation, multi-organ failure, anaphylaxis, any auto-immune disorder, cytokine-release syndrome, intestinal bleeding, renal failure, proteinuria, thromboembolic events, stroke, heart failure, or vasculitis according to the National Cancer Institute Common Terminology Criteria for Adverse Events (CTCAE).

Secondary endpoints, which assess the efficacy of the experimental vaccine to elicit a specific immune response to VEGFR-2, included the number of immune positive patients.

A further secondary endpoint was the clinical response: Tumor staging according to the response evaluation criteria in solid tumors (RECIST), overall response rate, progression free survival, overall survival, and changes in tumor perfusion. Tumor perfusion was determined by dynamic contrast-enhanced Magnetic Resonance Imaging (DCE-MRI) on a 1.5 Tesla system (Magnetom Aera, Siemens, Erlangen, Germany).

VXM01 had been manufactured according to Good Manufacturing Practice (GMP) and was given in a buffered solution. The placebo control consisted of isotonic sodium chloride solution.

Patient Selection and Clinical Study Design:

The study included a maximum of 45 patients with either locally advanced and inoperable or stage IV pancreatic cancer. The eligibility criteria are summarized in Table 1.

TABLE 1

Inclusion Criteria

1. Written informed consent, signed and dated
2. Locally advanced, inoperable and stage IV pancreatic cancer patients according to UICC based on diagnostic imaging using computer-tomography (CT) or histological examinations
3. Male or post-menopausal female
4. Age ≥ 18 years
5. Chemotherapy naive within 60 days before screening visit except gemcitabine treatment
6. Karnofsky index > 70
7. Life expectancy > 3 months
8. Adequate renal, hepatic, and bone marrow function
9. Absolute neutrophil count > 1500/μL
10. Hemoglobin > 10 g/dL
11. Platelets > 75000/μL TABLE 1-continued 12. Prothrombin time and international normalized ratio (INR) < 1.5 times upper limit of normal (ULN) (except under anticoagulant treatment)
13. Aspartate aminotransferase < 4 times ULN
14. Alanine aminotransferase < 4 times ULN
15. Total bilirubin < 3 times ULN
16. Creatinine clearance estimated according to Cockcroft-Gault > 30 mL/min
17. Proteinuria < 1 g protein on 24 h urine collection Exclusion Criteria 18. State after pancreas resection (complete or partial)
19. Resectable disease
20. Drug trial participation within 60 days before screening visit
21. Other previous or current malignancy except basal or squamous cell skin cancer, in situ cervical cancer, or any other cancer from which the patient has been disease-free for < 2 years
22. Prior vaccination with Ty21a State after pancreas resection (complete or partial)
23. Resectable disease
24. Drug trial participation within 60 days before screening visit
25. Other previous or current malignancy except basal or squamous cell skin cancer, in situ cervical cancer, or any other cancer from which the patient has been disease-free for < 2 years
26. Prior vaccination with Ty21a
27. Cardiovascular disease defined as:
    Uncontrolled hypertension (systolic blood pressure > 160 mmHg or diastolic blood pressure > 100 mmHg)
    Arterial thromboembolic event within 6 months before randomization including:
        Myocardial infarction
        Unstable angina pectoris
        Cerebrovascular accident
        Transient ischemic attack
28. Congestive heart failure New York Heart Association grade III to IV
29. Serious ventricular arrhythmia requiring medication
30. Clinically significant peripheral artery disease > grade 2b according to Fontaine
31. Hemoptysis within 6 months before randomization
32. Esophageal varices
33. Upper or lower gastrointestinal bleeding within 6 months before randomization
34. Significant traumatic injury within 4 weeks before randomization
35. Non-healing wound, bone fracture or any history of gastrointestinal ulcers within three years before inclusion, or positive gastroscopy within 3 months before inclusion
36. Gastrointestinal fistula
37. Thrombolysis therapy within 4 weeks before randomization
38. Bowel obstruction within the last 30 days before screening visit
39. Liver cirrhosis ≥ grade B according to Child-Pugh Score-Classification
40. Presence of any acute or chronic systemic infection
41. Radiotherapy within 4 weeks before randomization
42. Major surgical procedures, or open biopsy within 4 weeks before randomization
43. Fine needle aspiration within 7 days before randomization
44. Chronic concurrent therapy within 2 weeks before and during the double-blind study period with:
    Corticosteroids (except steroids for adrenal failure) or immunosuppressive agents
    Antibiotics
    Bevacizumab
    Any epidermal growth factor receptor inhibitor
45. Chemotherapy except gemcitabine before Day 10 Multi-drug resistant gram-negative germ
46. Pregnancy
47. Lactation
48. Inability to comply with study and/or follow-up procedures
49. History of other disease, metabolic dysfunction, physical examination finding, or clinical laboratory finding giving reasonable suspicion of a disease or condition that contraindicates the use of an investigational drug or that might affect the interpretation of the study results or render the patient at high risk for treatment complications
50. Women of childbearing potential
51. Any history of drug hypersensitivity
52. Any condition which results in an undue risk for the patient during the study participation according to the investigator A total of 371 patients were screened for the study. 326 patients were ineligible because of excluded medical therapies (179), preexisting medical conditions (129) in patient's medical history and personal reasons (18). 45 patients were enrolled, randomized and completed successfully the 10 days in-house study phase at the Clinical Research Unit at the University Clinics of Heidelberg (KliPS), in line with the study protocol. Demographic baseline disease characteristics of the patients were not significantly different in the two groups, but time since diagnosis was longer in the VXM01 group (8 vs. 6 months) and patients in the VXM01 group had a more advanced tumor stage at the time of inclusion (CA19.9>1000 in 40% vs. 20% and metastatic disease in 83% vs. 53%).

Male and postmenopausal female patients were enrolled in this study. However, differences between the two genders were not investigated. The average survival time of the patients participating in this trial was under 6 months. However, the follow-up period for the patients as defined per protocol was up to 24 months. The study treatment was given first-line as an add-on to standard of care. Taking further into account other factors, among them the multiple primary and secondary pharmacodynamic preclinical studies, the risk-benefit analysis was assumed to have a favorable result for the patient population selected.

Figure 3:
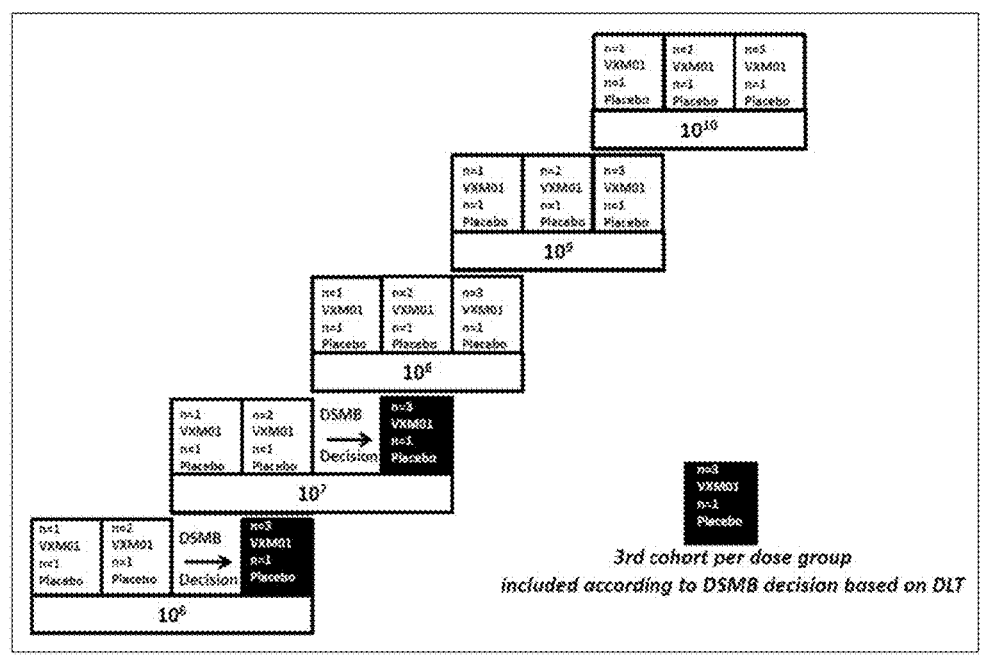

The starting dose consisted of a solution containing $10^6$ colony forming units (CFU) of VXM01 or placebo. This VXM01 dose was chosen for safety reasons and was assumed to be below the minimal effective dose to elicit an immune response. For comparison, one dose of Typhoral, the licensed vaccine against typhoid fever, contains $2 \times 10^9$ to $6 \times 10^9$ CFU of *Salmonella typhi* Ty21a, equivalent to approximately thousand times the VXM01 starting dose. The dose was escalated in factor-of-ten logarithmic steps, which appears to be justified for a live bacterial vaccine. The dose escalating design is depicted in FIG. 3.

Complying with guidelines for first in human trials, the patients of one dose group were treated in cohorts. The first administration of VXM01 in any dose group was given to one patient only accompanied by one patient receiving placebo. The second cohort of each dose group consisted of two patients receiving VXM01 and one patient receiving placebo. This staggered administration with one front-runner, i.e. only one patient receiving VXM01 first, served to mitigate the risks.

A third cohort of patients (three receiving VXM01 and one receiving placebo) were included in the $10^8$, $10^9$, and $10^{10}$ dose groups. This approach minimized exposure to VXM01 doses assumed to be sub-therapeutic. The third cohort and the first two cohorts of the next higher treatment group were treated in parallel based on a clearly defined randomization strategy. This strategy allowed for recruitment of available patients and avoided selection bias for patients treated in parallel in the lower and higher dose group. In the $10^6$ and $10^7$ dose groups, a third cohort of patients was included only if one patient out of the initial three patients receiving VXM01 of the respective dose group experienced a DLT and required confirmation by a decision of the Data Safety Monitoring Board (DSMB).

All patients completed the seven day vaccination course of 4 doses every second day in line with the protocol without any dose reduction. Because of no observed dose limiting toxicities (DLT) the maximum tolerated dose was not reached. VXM01 was well tolerated at all dose levels. AEs and SAEs where equally distributed among both groups and there were no obvious signs for dose-dependent side effects among the groups.

The environmental risk inherent to an oral vaccine is the potential of excretion to the environment and subsequent vaccination of people outside the target population. All study patients were confined in the study site (KliPS) for the period during which vaccinations took place plus three additional days. All feces of study patients were collected and incinerated. Body fluids and feces samples were investigated for VXM01 shedding. Fecal excretion of VXM01 was observed in two patients, one in the $10^9$ and one in the $10^{10}$ dose group. VXM01 excretion in feces in both patients was transient at one occasion after the first or second administration, respectively, and disappeared without antibiotic treatment. In other body fluids, no excretion was determined.

Hygienic precautions were applied to protect study personnel from accidental uptake. Study personnel was trained specifically for this aspect of the study.

Patients were only discharged from hospital, if they tested negative for excretion of the vaccine after the last administration of the study drug. In case a patient tested positive for excretion after the last administration, an antibiotic decontamination of the gastrointestinal tract was conducted before the patient was discharged. Excretion was followed up until results were negative. These measures appear to have been justified and sufficient to protect the environment and study personnel from exposure to VXM01 until the shedding profile had been elucidated.

Figure 4:
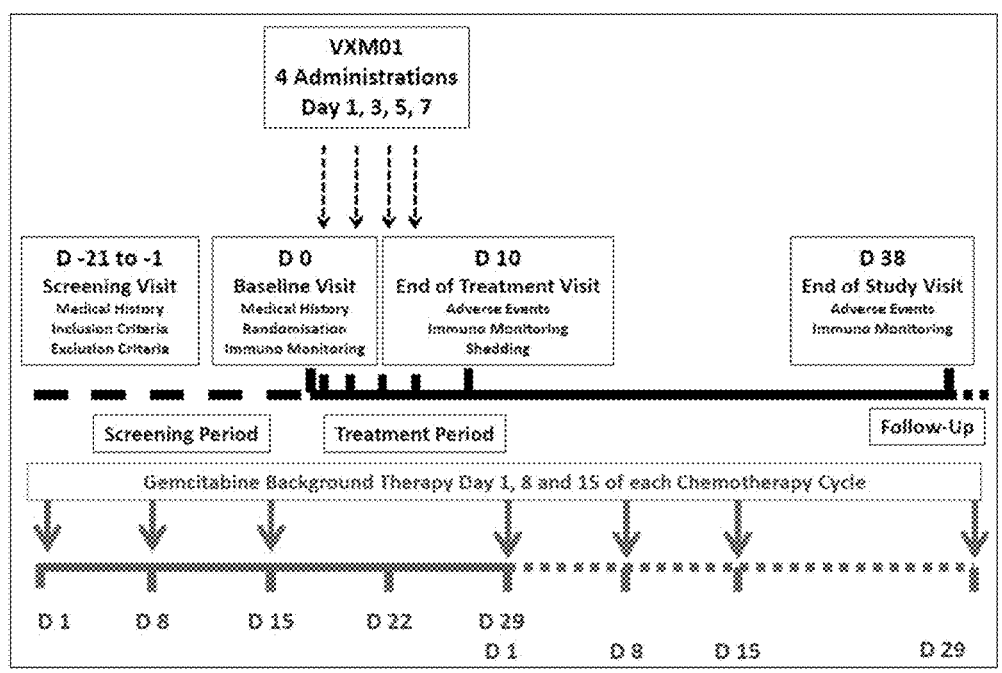

VXM01 was applied in parallel to the gemcitabine background therapy as shown in FIG. 4 (overall study scheme). In brief, gemcitabine was given on days 1, 8, and 15 of a 28 days chemotherapy cycle. The vaccine was given four times on days 1, 3, 5, and 7, starting three days after the last dose of gemcitabine. The double blinded phase of the study ended 31 days after the last patient had received the last administration.

For this phase I trial (advanced or stage IV pancreatic cancer patients) a patient population with dismal prognosis and the relatively gentle standard of care with regard to immunosuppression was chosen. Co-regimes of the chemotherapeutic agent gemcitabine with tumor vaccination may be synergistic. In addition, specific T-cell activation was measured in this patient setting demonstrating effectiveness of the vaccine VXM01. A placebo control was included in the present trial, in order to gain further knowledge on specific safety issues related to the active vaccine vs. the background treatment. In addition, the pooled placebo patients served as a sound comparator for assessing specific immune activation and other signs of clinical efficacy. If and when moving into phase II, a different patient entity with a longer life expectancy can be envisaged depending on the observed safety profile. Such studies will also include tumor types that have shown to be more susceptible to anti-angiogenic treatment.

Example 3 VXM01 Specific T-Cell Responses

Responses to VXM01 were assessed by monitoring the frequencies of VEGFR2 specific T-cells in peripheral blood of VXM01 and placebo treated patients, detected by INFγ ELISpot, at different time points prior during and post vaccination.

Firstly, T-cells and peptide pulsed DC were added to wells coated with anti-INFγ antibodies. After a period of incubation, cells were removed with secreted INFγ left binding with the coat antibodies. Then detection antibody was added to detect the bound INFγ, and after a signal amplification, the final yield could be viewed as "color spots" representing single activated and specific T-cells.

Positivity of ELISpot samples was graded according to predefined rules defining signal increase resulting in grade 0 to 3 per sample:
No increase: grade 0
Clear increase but <3×: grade 1
≥3× but <5× increase: grade 2
≥5× increase: grade 3

The ELISpot immune response of study patients is depicted in Table 2:

TABLE 2

| VEGFR-2 specific T-cell response (Patients w/grading score ≥ 3) | | | | | |
|---|---|---|---|---|---|
| Placebo | $10^6$ CFUs/admin | $10^7$ CFUs/admin | $10^8$ CFUs/admin | $10^9$ CFUs/admin | $10^{10}$ CFUs/admin |
| 1/11 | 2/6 | 3/5 | 1/6 | 0/6 | 2/6 |

Figure 5:
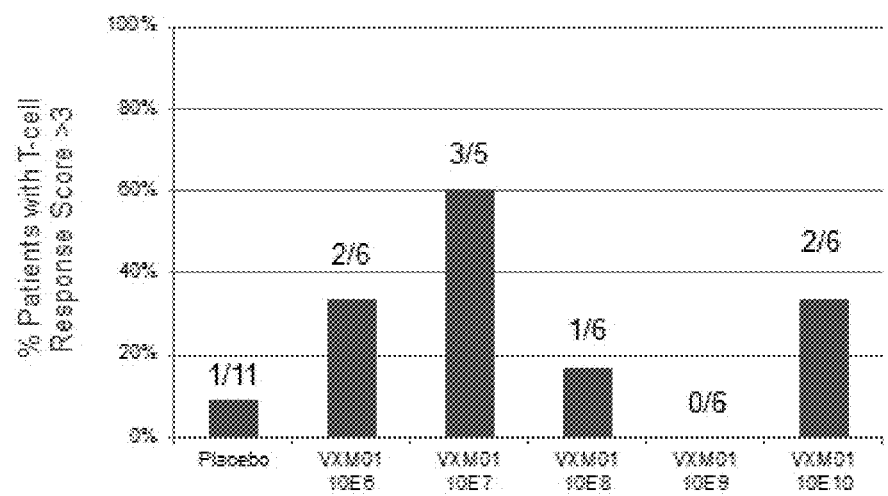

The results of the ELISpot immune response of study patients is graphically depicted in FIG. 5.

Example 4 Effects on Tumor Perfusion

Tumor perfusion was evaluated by contrast media transit time (Ktrans) during dynamic contrast enhanced magnetic resonance imaging (DCEMRI) to characterize treatment response. Dynamic Contrast-Enhanced T1—weighted imaging was performed. DCE—MRI was assessed on a 1.5 Tesla System (Magnetom Aera, Siemens, Erlangen, Germany) on day 0, 38 and 3 months after treatment. Dynamic contrast—enhanced MR-imaging was performed with VIBE (volumetric interpolated breath-hold) sequences. For that purpose, a dose of 8 ml Gadovist was injected.

For every examination, regions of interest were manually drawn within the tumor-tissue followed by pixel-by-pixel analysis using a Siemens software package (Tissue 4D). ROI-modeling was based on the Tofts model with assumed T10 (1000 ms) and Parker AIF. For the estimation of tumor-perfusion Ktrans was regarded as primary endpoint.

Mean changes in tumor perfusion were −9% in the VXM01 group (n=26) vs. +18% in the placebo group (n=11). A greater than 33% drop in tumor perfusion was detected in 35% of evaluable VXM01 treated patients vs. 10% in the placebo group. The strongest responders were further analyzed in a subgroup analysis. Maximum average effects were detected at the d38 time point. The effects of various doses of VXM01 on tumor perfusion are graphically depicted in FIG. 6.

Example 5 Biomarkers of Angiogenesis

In order to further characterize the VEGFR-2 specific T-cell mediated, anti-angiogenic activity of VXM01, accompanying changes in angiogenesis biomarkers VEGF A, human collagen IV and blood pressure were monitored.
VEGF A:

VEGF A was measured in human serum samples by ELISA using a commercial assay kit (ELISA Kit Quantikine Human VEGF A Immunoassay, R&D Systems, Cat.-No.: DVE00). The assay was used as described in the package insert and as modified as part of this study plan according to the foregoing validation study 580.132.2786.

This assay employs the quantitative sandwich enzyme immunoassay technique. A monoclonal antibody specific for human VEGF A had been pre-coated onto a microplate. Standards, quality controls (commercially obtained) and samples were pipetted into the wells and any VEGF A present was bound by the immobilized antibody. Calibrator, quality control samples, and samples were analyzed as duplicates. After washing away any unbound substances, an enzyme-linked polyclonal antibody specific for VEGF A was added to the wells. Following a wash to remove any unbound antibody-enzyme reagent, a substrate solution was added to the wells and color developed in proportion to the amount of VEGF A bound in the initial step. The color development was stopped and the intensity of the color was measured using a spectrophotometric microtiter plate reader at 450 nm. A standard curve was generated by plotting the absorbance versus the respective VEGF A concentration for each standard. The concentration of VEGF A in the sample was determined directly from this curve.

VEGF-A serum levels increased in the VXM01 group by 235% on both d38 and m3 vs. 17% and 31% in the placebo group (p=0.05 at m3). The quantification of VEGF A in patient serum samples is graphically depicted in FIG. 7.
Collagen IV:

Human Collagen IV was measured in human serum samples by ELISA using a commercial assay kit (Human Collagen IV ELISA, Serum, KAMIYA BIOMEDICAL COMPANY, Cat.-No.: KT-035). The assay was used as described in the package insert and as modified as part of this study report according to the foregoing validation study 580.132.3645.

The human Collagen IV ELISA was a solid phase one-step sandwich ELISA. Collagen IV in the sample was bound simultaneously by a solid phase monoclonal antibody and a monoclonal antibody-enzyme conjugate, each directed at different antigenic sites. This resulted in the collagen IV molecule being sandwiched between the solid phase and enzyme-labeled antibodies. After removing unbound enzyme-labeled antibody and sample, the plate was incubated with chromogenic substrate (TMB). The resultant color development was directly proportional to the amount of collagen IV in the sample.

Serum levels of collagen IV increased on d38 and m3 in average by 7% and 22%, respectively, in the VXM01 group vs. changes of 2% and −7% in the placebo group (p=0.02 at m3). The quantification of collagen IV in patient serum samples is graphically depicted in FIG. 8.
Blood Pressure:

Blood pressure (systolic and diastolic) and pulse rate as pharmacodynamic markers of anti-angiogenic efficacy were measured after 5 minutes rest in supine position. Average systolic blood pressure changes were +3.6 mmHg and +3.9 mmHg in the treatment group vs. −8.8 mHg and 9.1 mmHg under placebo (p=0.08 at d38). Effects on average blood pressure after the first vaccination dose (up to day 38) are graphically depicted in FIG. 9.

Example 6 Anti-Carrier Immunity

In order to assess immune responses to the bacterial vehicle, anti-*Salmonella typhi* IgG and IgM immunoglobulins were detected by ELISA using two commercial assay kits (*Salmonella typhi* IgG ELISA, Cat. No. ST0936G and *Salmonella typhi* IgM ELISA, Cat. No. ST084M, Calbiotech. Inc., 10461 Austin Dr, Spring Valley, Calif. 91978, USA). These assays were qualitative assays. The assays were used as described in the package inserts respectively App. I/I) and as modified as part of the study plan according to the foregoing validation study 580.132.2785.

Both assays employed the enzyme-linked immunosorbent assay technique. Calibrator, negative control, positive control and samples were analyzed as duplicates. Diluted patient serum (dilution 1:101) was added to wells coated with purified antigen. IgG or IgM specific antibody, if present, bound to the antigen. All unbound materials were washed away and the enzyme conjugate was added to bind to the antibody-antigen complex, if present. Excess enzyme conjugate was washed off and substrate was added. The plate was incubated to allow for hydrolysis of the substrate by the enzyme. The intensity of the color generated was proportional to the amount of IgG or IgM specific antibody in the sample. The intensity of the color was measured using a spectrophotometric microtiter plate reader at 450 nm. The cut off was calculated as follows:

Calibrator OD×Calibrator Factor (CF).

The antibody index of each determination was determined by dividing the OD value of each sample by cut-off value.
Antibody Index Interpretation:

| | |
|---|---|
| <0.9 | No detectable antibody to Salmonella typhi IgG or IgM by ELISA |
| 0.9-1.1 | Borderline positive |
| >1.1 | Detectable antibody to Salmonella typhi IgG or IgM by ELISA |

Figure 10:
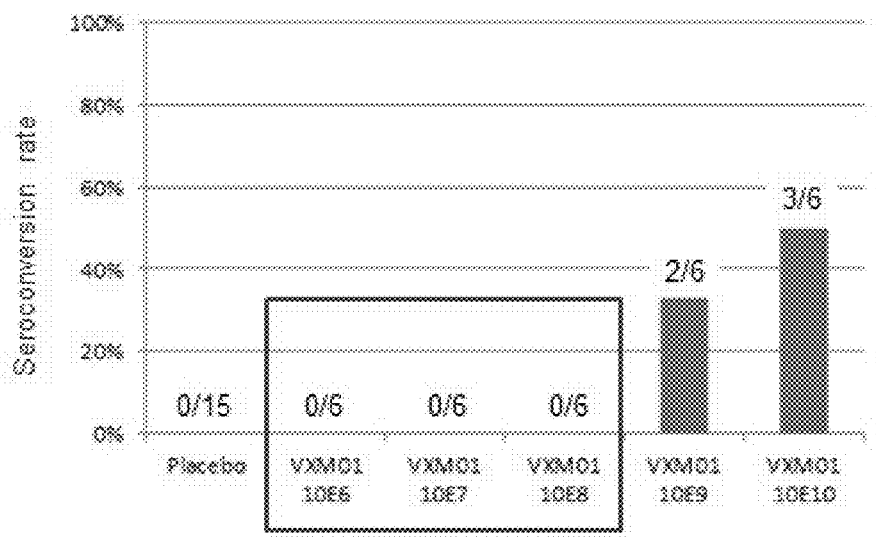

The number of patients with detectable anti-*Salmonella typhi* IgG immunoglobulins are depicted in FIG. 10.

Example 7 Excretion

The shedding of bacteria in stool and body fluids, tears, saliva, urine and blood was monitored in the study VXM01-01-DE according to methods validated transferred as formerly validated according to GLP at an established central service laboratory (Huntingdon Life Sciences, Huntingdon, UK). Shedding and biodistribution in body fluids of VXM01 were determined by plate and enrichment cultivation. Identity of the VXM01 carrier bacterium was determined by serological agglutination and PCR methods.

Test samples (blood, tears, urine, saliva and faeces) were collected at the site in Heidelberg and same-day delivery of post-vaccination samples took place to MicroMol GmbH located in Karlsruhe, Germany. The bacterial vector shedding and biodistribution analysis cascade was designed to detect live CFU of VXM01 or horizontal plasmid transfer. It consists of two separate analysis branches (Branch I and Branch II):
Branch I: Plating method to detect any horizontal plasmid transfer
Branch II: Liquid enrichment culture to detect live CFU of VXM01

The analysis cascade is followed by a matrix decision in order to determine the excretion of live bacteria VXM01 or observation of a horizontal plasmid transfer. The cascade is outlined in FIG. 11.
Analysis Branch I for detection of horizontal plasmid transfer:
    Day 0: Plating of the 5 test samples on 3 TSA (+kanamycin) plates each, incubation over night at 37° C.
    Day 1: Visual discrimination between VXM01 (Ty21a) and non-VXM01 morphotypes on the selective plates. Selection of non-VXM01 morphotypes (9 colonies each), streaking on agar plates (+kanamycin) for agglutination and parallel liquid culture (+kanamycin) for each pooled morphotype for PCR analysis the following day
    Day 2: PCR of each liquid morphotype pool
Analysis Branch II for detection of VXM01:
    Day 0: Preparation of liquid enrichment cultures (+kanamycin) for each of the 5 test samples
    Day 1: Direct PCR on each liquid enrichment culture. Streaking of each enrichment culture on agar plates (+kanamycin) for serological analysis the following day in case PCR is positive for plasmid
    Day 2: Serological confirmation of presence of VXM01 (Ty21a)

Due to the fact that PCR of any test sample would not be discriminative between live CFU and/or free-floating plasmid or Ty21a genomic DNA and as agglutination cannot be applied directly on test samples, PCR as well as agglutination methods were used as second-line methods after plating method was applied. Identified live colonies grown on kanamycin-containing plates were further characterized by these methods. Only the plating method enables discrimination between live and dead cells (either VXM01 or foreign non-VXM01 plasmid transformants due to horizontal plasmid transfer).

Fecal excretion of VXM01 was observed in two patients, one in the $10^9$ and one in the $10^{10}$ dose group. VXM01 excretion in feces in both patients was transient at one occasion after the first or second administration, respectively, and disappeared without antibiotic treatment. The numbers of VMX01 excreting patients in the various dose groups are graphically depicted in FIG. 12.

In summary, VXM01 has the potential to target a variety of tumor types and to overcome multiple hurdles encountered by other present cancer vaccine approaches. A tempting vision is the possibility of combining the vaccine of the present invention with a multitude of other anti-cancer and immune-modulatory agents. The results of the here presented study motivate the inventors to move forward this highly interesting approach.

The invention claimed is:

1. A method of providing cancer immunotherapy comprising administering to a patient suffering from a cancer, a DNA vaccine comprising an attenuated mutant strain of *Salmonella typhi* Ty21a comprising an expression cassette encoding a human VEGFR-2 having the amino acid sequence of SEQ ID NO 1, wherein a single dose of the vaccine is $10^9$ colony forming units (CFU) or less than $10^9$ CFU.

2. The method of claim 1, wherein the expression cassette is a eukaryotic expression cassette.

3. The method of claim 2, wherein the cancer immunotherapy is an anti-angiogenic cancer immunotherapy and wherein the DNA vaccine comprises the attenuated *Salmonella typhi* strain Ty21a transformed by a plasmid that contains the DNA encoding the VEGFR-2 protein of SEQ ID NO 1.

4. The method of claim 3, wherein the plasmid is the 7580 bp pVAX10.VR2-1 having the sequence of SEQ ID NO 3.

5. The method of claim 1, wherein the cancer is pancreatic cancer.

6. The method of claim 5, wherein said pancreatic cancer is stage IV or locally advanced pancreatic cancer.

7. The method of claim 1, wherein the cancer includes metastases.

8. The method of claim 1, further comprising administering to the patient chemotherapy and/or radiotherapy.

9. The method of claim 8, wherein the chemotherapeutic agent is gemcitabine.

10. The method of claim 8, wherein the administration of the DNA vaccine is carried out during the chemotherapy treatment cycle.

11. The method of claim 1, wherein the DNA vaccine is administered orally.

12. The method of claim 1, wherein the single dose of the vaccine is a dose selected from the group of: $1 \times 10^5$, $1 \times 10^6$, $1 \times 10^7$, $1 \times 10^8$, and $1 \times 10^9$ CFU.

13. The method of claim 1, wherein the single dose of the vaccine is less than $1 \times 10^9$ CFU.

14. The method of claim 1, wherein the single dose of the vaccine is less than $1 \times 10^8$ CFU.

15. The method of claim 1, wherein the single dose of the vaccine comprises from $10^6$ to $10^9$ CFU.

16. A method of providing cancer immunotherapy to a cancer patient comprising administering to the patient a DNA vaccine VXM01, comprising the attenuated *Salmonella typhi* strain Ty21a transformed by a 7580 bp plasmid, the plasmid comprising a DNA encoding the VEGFR-2 protein of SEQ ID NO 1 under the control of a CMV promoter, the kanamycin resistance gene, and the pMB1 ori, and is designated as pVAX10.VR2-1, and wherein a single dose of the vaccine is $10^9$ CFU or less than $10^9$ CFU.

17. The method of claim 1, wherein the single dose of the vaccine comprises from $10^6$ to $10^8$ CFU.

18. The method of claim 1, wherein the method further comprises administering to the patient one or more further attenuated mutant strains(s) of *Salmonella typhi* Ty21a comprising a eukaryotic expression cassette encoding a tumor antigen and/or a tumor stroma antigen.

* * * * *

SEQUENCE LISTING

```
<160> NUMBER OF SEQ ID NOS: 3

<210> SEQ ID NO 1
<211> LENGTH: 1356
<212> TYPE: PRT
<213> ORGANISM: Homo sapiens

<400> SEQUENCE: 1

Met Gln Ser Lys Val Leu Leu Ala Val Ala Leu Trp Leu Cys Val Glu
1               5                   10                  15

Thr Arg Ala Ala Ser Val Gly Leu Pro Ser Val Ser Leu Asp Leu Pro
            20                  25                  30
```

```
Arg Leu Ser Ile Gln Lys Asp Ile Leu Thr Ile Lys Ala Asn Thr Thr
            35                  40                  45

Leu Gln Ile Thr Cys Arg Gly Gln Arg Asp Leu Asp Trp Leu Trp Pro
 50                  55                  60

Asn Asn Gln Ser Gly Ser Glu Gln Arg Val Glu Val Thr Glu Cys Ser
 65                  70                  75                  80

Asp Gly Leu Phe Cys Lys Thr Leu Thr Ile Pro Lys Val Ile Gly Asn
                 85                  90                  95

Asp Thr Gly Ala Tyr Lys Cys Phe Tyr Arg Glu Thr Asp Leu Ala Ser
                100                 105                 110

Val Ile Tyr Val Tyr Val Gln Asp Tyr Arg Ser Pro Phe Ile Ala Ser
                115                 120                 125

Val Ser Asp Gln His Gly Val Val Tyr Ile Thr Glu Asn Lys Asn Lys
130                 135                 140

Thr Val Val Ile Pro Cys Leu Gly Ser Ile Ser Asn Leu Asn Val Ser
145                 150                 155                 160

Leu Cys Ala Arg Tyr Pro Glu Lys Arg Phe Val Pro Asp Gly Asn Arg
                165                 170                 175

Ile Ser Trp Asp Ser Lys Lys Gly Phe Thr Ile Pro Ser Tyr Met Ile
                180                 185                 190

Ser Tyr Ala Gly Met Val Phe Cys Glu Ala Lys Ile Asn Asp Glu Ser
                195                 200                 205

Tyr Gln Ser Ile Met Tyr Ile Val Val Val Gly Tyr Arg Ile Tyr
                210                 215                 220

Asp Val Val Leu Ser Pro Ser His Gly Ile Glu Leu Ser Val Gly Glu
225                 230                 235                 240

Lys Leu Val Leu Asn Cys Thr Ala Arg Thr Glu Leu Asn Val Gly Ile
                245                 250                 255

Asp Phe Asn Trp Glu Tyr Pro Ser Ser Lys His Gln His Lys Lys Leu
                260                 265                 270

Val Asn Arg Asp Leu Lys Thr Gln Ser Gly Ser Glu Met Lys Lys Phe
                275                 280                 285

Leu Ser Thr Leu Thr Ile Asp Gly Val Thr Arg Ser Asp Gln Gly Leu
                290                 295                 300

Tyr Thr Cys Ala Ala Ser Ser Gly Leu Met Thr Lys Lys Asn Ser Thr
305                 310                 315                 320

Phe Val Arg Val His Glu Lys Pro Phe Val Ala Phe Gly Ser Gly Met
                325                 330                 335

Glu Ser Leu Val Glu Ala Thr Val Gly Glu Arg Val Arg Ile Pro Ala
                340                 345                 350

Lys Tyr Leu Gly Tyr Pro Pro Pro Glu Ile Lys Trp Tyr Lys Asn Gly
                355                 360                 365

Ile Pro Leu Glu Ser Asn His Thr Ile Lys Ala Gly His Val Leu Thr
                370                 375                 380

Ile Met Glu Val Ser Glu Arg Asp Thr Gly Asn Tyr Thr Val Ile Leu
385                 390                 395                 400

Thr Asn Pro Ile Ser Lys Glu Lys Gln Ser His Val Val Ser Leu Val
                405                 410                 415

Val Tyr Val Pro Pro Gln Ile Gly Glu Lys Ser Leu Ile Ser Pro Val
                420                 425                 430

Asp Ser Tyr Gln Tyr Gly Thr Thr Gln Thr Leu Thr Cys Thr Val Tyr
                435                 440                 445
```

```
Ala Ile Pro Pro Pro His His Ile His Trp Tyr Trp Gln Leu Glu Glu
    450                 455                 460

Glu Cys Ala Asn Glu Pro Ser Gln Ala Val Ser Val Thr Asn Pro Tyr
465                 470                 475                 480

Pro Cys Glu Glu Trp Arg Ser Val Asp Phe Gln Gly Gly Asn Lys
                485                 490                 495

Ile Glu Val Asn Lys Asn Gln Phe Ala Leu Ile Glu Gly Lys Asn Lys
                500                 505                 510

Thr Val Ser Thr Leu Val Ile Gln Ala Ala Asn Val Ser Ala Leu Tyr
        515                 520                 525

Lys Cys Glu Ala Val Asn Lys Val Gly Arg Gly Glu Arg Val Ile Ser
530                 535                 540

Phe His Val Thr Arg Gly Pro Glu Ile Thr Leu Gln Pro Asp Met Gln
545                 550                 555                 560

Pro Thr Glu Gln Glu Ser Val Ser Leu Trp Cys Thr Ala Asp Arg Ser
                565                 570                 575

Thr Phe Glu Asn Leu Thr Trp Tyr Lys Leu Gly Pro Gln Pro Leu Pro
                580                 585                 590

Ile His Val Gly Glu Leu Pro Thr Pro Val Cys Lys Asn Leu Asp Thr
        595                 600                 605

Leu Trp Lys Leu Asn Ala Thr Met Phe Ser Asn Ser Thr Asn Asp Ile
    610                 615                 620

Leu Ile Met Glu Leu Lys Asn Ala Ser Leu Gln Asp Gln Gly Asp Tyr
625                 630                 635                 640

Val Cys Leu Ala Gln Asp Arg Lys Thr Lys Lys Arg His Cys Val Val
                645                 650                 655

Arg Gln Leu Thr Val Leu Glu Arg Val Ala Pro Thr Ile Thr Gly Asn
            660                 665                 670

Leu Glu Asn Gln Thr Thr Ser Ile Gly Glu Ser Ile Glu Val Ser Cys
        675                 680                 685

Thr Ala Ser Gly Asn Pro Pro Pro Gln Ile Met Trp Phe Lys Asp Asn
690                 695                 700

Glu Thr Leu Val Glu Asp Ser Gly Ile Val Leu Lys Asp Gly Asn Arg
705                 710                 715                 720

Asn Leu Thr Ile Arg Arg Val Arg Lys Glu Asp Glu Gly Leu Tyr Thr
                725                 730                 735

Cys Gln Ala Cys Ser Val Leu Gly Cys Ala Lys Val Glu Ala Phe Phe
            740                 745                 750

Ile Ile Glu Gly Ala Gln Glu Lys Thr Asn Leu Glu Ile Ile Ile Leu
        755                 760                 765

Val Gly Thr Ala Val Ile Ala Met Phe Phe Trp Leu Leu Leu Val Ile
    770                 775                 780

Ile Leu Arg Thr Val Lys Arg Ala Asn Gly Gly Glu Leu Lys Thr Gly
785                 790                 795                 800

Tyr Leu Ser Ile Val Met Asp Pro Asp Glu Leu Pro Leu Asp Glu His
                805                 810                 815

Cys Glu Arg Leu Pro Tyr Asp Ala Ser Lys Trp Glu Phe Pro Arg Asp
            820                 825                 830

Arg Leu Lys Leu Gly Lys Pro Leu Gly Arg Gly Ala Phe Gly Gln Val
        835                 840                 845

Ile Glu Ala Asp Ala Phe Gly Ile Asp Lys Thr Ala Thr Cys Arg Thr
850                 855                 860
```

```
Val Ala Val Lys Met Leu Lys Glu Gly Ala Thr His Ser Glu His Arg
865                 870                 875                 880

Ala Leu Met Ser Glu Leu Lys Ile Leu Ile His Ile Gly His His Leu
                885                 890                 895

Asn Val Val Asn Leu Leu Gly Ala Cys Thr Lys Pro Gly Gly Pro Leu
            900                 905                 910

Met Val Ile Val Glu Phe Cys Lys Phe Gly Asn Leu Ser Thr Tyr Leu
        915                 920                 925

Arg Ser Lys Arg Asn Glu Phe Val Pro Tyr Lys Thr Lys Gly Ala Arg
    930                 935                 940

Phe Arg Gln Gly Lys Asp Tyr Val Gly Ala Ile Pro Val Asp Leu Lys
945                 950                 955                 960

Arg Arg Leu Asp Ser Ile Thr Ser Ser Gln Ser Ser Ala Ser Ser Gly
                965                 970                 975

Phe Val Glu Glu Lys Ser Leu Ser Asp Val Glu Glu Glu Glu Ala Pro
            980                 985                 990

Glu Asp Leu Tyr Lys Asp Phe Leu Thr Leu Glu His Leu Ile Cys Tyr
        995                 1000                1005

Ser Phe Gln Val Ala Lys Gly Met Glu Phe Leu Ala Ser Arg Lys
    1010                1015                1020

Cys Ile His Arg Asp Leu Ala Ala Arg Asn Ile Leu Leu Ser Glu
    1025                1030                1035

Lys Asn Val Val Lys Ile Cys Asp Phe Gly Leu Ala Arg Asp Ile
    1040                1045                1050

Tyr Lys Asp Pro Asp Tyr Val Arg Lys Gly Asp Ala Arg Leu Pro
    1055                1060                1065

Leu Lys Trp Met Ala Pro Glu Thr Ile Phe Asp Arg Val Tyr Thr
    1070                1075                1080

Ile Gln Ser Asp Val Trp Ser Phe Gly Val Leu Leu Trp Glu Ile
    1085                1090                1095

Phe Ser Leu Gly Ala Ser Pro Tyr Pro Gly Val Lys Ile Asp Glu
    1100                1105                1110

Glu Phe Cys Arg Arg Leu Lys Glu Gly Thr Arg Met Arg Ala Pro
    1115                1120                1125

Asp Tyr Thr Thr Pro Glu Met Tyr Gln Thr Met Leu Asp Cys Trp
    1130                1135                1140

His Gly Glu Pro Ser Gln Arg Pro Thr Phe Ser Glu Leu Val Glu
    1145                1150                1155

His Leu Gly Asn Leu Leu Gln Ala Asn Ala Gln Gln Asp Gly Lys
    1160                1165                1170

Asp Tyr Ile Val Leu Pro Ile Ser Glu Thr Leu Ser Met Glu Glu
    1175                1180                1185

Asp Ser Gly Leu Ser Leu Pro Thr Ser Pro Val Ser Cys Met Glu
    1190                1195                1200

Glu Glu Glu Val Cys Asp Pro Lys Phe His Tyr Asp Asn Thr Ala
    1205                1210                1215

Gly Ile Ser Gln Tyr Leu Gln Asn Ser Lys Arg Lys Ser Arg Pro
    1220                1225                1230

Val Ser Val Lys Thr Phe Glu Asp Ile Pro Leu Glu Glu Pro Glu
    1235                1240                1245

Val Lys Val Ile Pro Asp Asp Asn Gln Thr Asp Ser Gly Met Val
    1250                1255                1260
```

| | | | | | | | | | | |
|---|---|---|---|---|---|---|---|---|---|---|
| Leu | Ala | Ser | Glu | Glu | Leu | Lys | Thr | Leu | Glu | Asp | Arg | Thr | Lys | Leu |
| | 1265 | | | | | 1270 | | | | | 1275 | | | |
| Ser | Pro | Ser | Phe | Gly | Gly | Met | Val | Pro | Ser | Lys | Ser | Arg | Glu | Ser |
| | 1280 | | | | | 1285 | | | | | 1290 | | | |
| Val | Ala | Ser | Glu | Gly | Ser | Asn | Gln | Thr | Ser | Gly | Tyr | Gln | Ser | Gly |
| | 1295 | | | | | 1300 | | | | | 1305 | | | |
| Tyr | His | Ser | Asp | Asp | Thr | Asp | Thr | Thr | Val | Tyr | Ser | Ser | Glu | Glu |
| | 1310 | | | | | 1315 | | | | | 1320 | | | |
| Ala | Glu | Leu | Leu | Lys | Leu | Ile | Glu | Ile | Gly | Val | Gln | Thr | Gly | Ser |
| | 1325 | | | | | 1330 | | | | | 1335 | | | |
| Thr | Ala | Gln | Ile | Leu | Gln | Pro | Asp | Ser | Gly | Thr | Thr | Leu | Ser | Ser |
| | 1340 | | | | | 1345 | | | | | 1350 | | | |
| Pro | Pro | Val | | | | | | | | | | | | |
| | 1355 | | | | | | | | | | | | | |

<210> SEQ ID NO 2
<211> LENGTH: 4071
<212> TYPE: DNA
<213> ORGANISM: Homo sapiens

<400> SEQUENCE: 2

| | |
|---|---|
| atgcagagca aggtgctgct ggccgtcgcc ctgtggctct gcgtggagac ccgggccgcc | 60 |
| tctgtgggtt tgcctagtgt ttctcttgat ctgcccaggc tcagcataca aaaagacata | 120 |
| cttacaatta aggctaatac aactcttcaa attacttgca ggggacagag ggacttggac | 180 |
| tggctttggc ccaataatca gagtggcagt gagcaagggg tggaggtgac tgagtgcagc | 240 |
| gatggcctct tctgtaagac actcacaatt ccaaaagtga tcggaaatga cactggagcc | 300 |
| tacaagtgct tctaccggga aactgacttg gcctcggtca tttatgtcta tgttcaagat | 360 |
| tacagatctc catttattgc ttctgttagt gaccaacatg gagtcgtgta cattactgag | 420 |
| aacaaaaaca aaactgtggt gattccatgt ctcgggtcca tttcaaatct caacgtgtca | 480 |
| ctttgtgcaa gatacccaga aaagagattt gttcctgatg taacagaatt ccctgggac | 540 |
| agcaagaagg gctttactat tcccagctac atgatcagct atgctggcat ggtcttctgt | 600 |
| gaagcaaaaa ttaatgatga agttaccag tctattatgt acatagttgt cgttgtaggg | 660 |
| tataggattt atgatgtggt tctgagtccg tctcatggaa ttgaactatc tgttggagaa | 720 |
| aagcttgtct taaattgtac agcaagaact gaactaaatg tggggattga cttcaactgg | 780 |
| gaatacccct tcttcgaagca tcagcataag aaacttgtaa accgagacct aaaaacccag | 840 |
| tctgggagtg agatgaagaa attttgagc accttaacta tagatggtgt aaccccggagt | 900 |
| gaccaaggat tgtacacctg tgcagcatcc agtgggctga tgaccaagaa gaacagcaca | 960 |
| tttgtcaggg tccatgaaaa accttttgtt gcttttggaa gtggcatgga atctctggtg | 1020 |
| gaagccacgg tggggagcg tgtcagaatc cctgcgaagt accttggtta cccaccccca | 1080 |
| gaaataaaat ggtataaaaa tggaatacc cttgagtcca atcacacaat taagcgggg | 1140 |
| catgtactga cgattatgga agtgagtgaa agagacacag gaaattacac tgtcatcctt | 1200 |
| accaatccca tttcaaagga gaagcagagc catgtggtct ctctggttgt gtatgtccca | 1260 |
| ccccagattg gtgagaaatc tctaatctct cctgtggatt cctaccagta cggcaccact | 1320 |
| caaacgctga catgtacggt ctatgccatt cctcccccgc atcacatcca ctggtattgg | 1380 |
| cagttggagg aagagtgcgc caacgagccc agcaagctg tctcagtgac aaacccatac | 1440 |
| ccttgtgaag aatggagaag tgtggaggac ttccagggag gaaataaaat tgaagttaat | 1500 |

-continued

```
aaaaatcaat ttgctctaat tgaaggaaaa aacaaaactg taagtaccct tgttatccaa      1560
gcggcaaatg tgtcagcttt gtacaaatgt gaagcggtca acaaagtcgg gagaggagag      1620
agggtgatct ccttccacgt gaccagggt cctgaaatta ctttgcaacc tgacatgcag       1680
cccactgagc aggagagcgt gtctttgtgg tgcactgcag acagatctac gtttgagaac      1740
ctcacatggt acaagcttgg cccacagcct ctgccaatcc atgtgggaga gttgcccaca      1800 cctgttttgca agaacttgga tactctttgg aaattgaatg ccaccatgtt ctctaatagc     1860
acaaatgaca ttttgatcat ggagcttaag aatgcatcct tgcaggacca aggagactat     1920
gtctgccttg ctcaagacag gaagaccaag aaaagacatt gcgtggtcag gcagctcaca      1980
gtcctagagc gtgtggcacc cacgatcaca ggaaacctgg agaatcagac gacaagtatt      2040
ggggaaagca tcgaagtctc atgcacggca tctgggaatc cccctccaca gatcatgtgg      2100
tttaaagata atgagaccct tgtagaagac tcaggcattg tattgaagga tgggaaccgg      2160
aacctcacta tccgcagagt gaggaaggag gacgaaggcc tctacacctg ccaggcatgc      2220
agtgttcttg gctgtgcaaa agtggaggca ttttttcataa tagaaggtgc ccaggaaaag     2280
acgaacttgg aaatcattat tctagtaggc acggcggtga ttgccatgtt cttctggcta     2340
cttcttgtca tcatcctacg gaccgttaag cgggccaatg gaggggaact gaagacaggc     2400
tacttgtcca tcgtcatgga tccagatgaa ctcccattgg atgaacattg tgaacgactg     2460
ccttatgatg ccagcaaatg ggaattcccc agagaccggc tgaagctagg taagcctctt     2520
ggccgtggtg cctttggcca agtgattgaa gcagatgcct ttggaattga caagacagca     2580
acttgcagga cagtagcagt caaaatgttg aagaaggag caacacacag tgagcatcga     2640
gctctcatgt ctgaactcaa gatcctcatt catattggtc accatctcaa tgtggtcaac     2700
cttctaggtg cctgtaccaa gccaggaggg ccactcatgg tgattgtgga attctgcaaa     2760
tttggaaacc tgtccactta cctgaggagc aagagaaatg aatttgtccc ctacaagacc     2820 aaagggcac gattccgtca agggaaagac tacgttggag caatcccctgt ggatctgaaa     2880 cggcgcttgg acagcatcac cagtagccag agctcagcca gctctggatt tgtggaggag     2940
aagtccctca gtgatgtaga agaagaggaa gctcctgaag atctgtataa ggacttcctg     3000
accttggagc atctcatctg ttacagcttc caagtggcta agggcatgga gttcttggca     3060
tcgcgaaagt gtatccacag ggaccctggcg gcacgaaata tcctcttatc ggagaagaac     3120
gtggttaaaa tctgtgactt tggcttggcc cgggatattt ataaagatcc agattatgtc    3180
agaaaaggag atgctcgcct ccctttgaaa tggatggccc cagaaacaat ttttgacaga     3240
gtgtacacaa tccagagtga cgtctggtct tttggtgttt tgctgtggga atatttttcc     3300
ttaggtgctt ctccatatcc tggggtaaag attgatgaag aattttgtag gcgattgaaa     3360
gaaggaacta gaatgagggc ccctgattat actacaccag aaatgtacca gaccatgctg     3420
gactgctggc acgggagcc cagtcagaga cccacgtttt cagagttggt ggaacatttg     3480
ggaaatctct tgcaagctaa tgctcagcag gatggcaaag actacattgt tcttccgata     3540
tcagagactt tgagcatgga agaggattct ggactctctc tgcctacctc acctgttttcc    3600 tgtatggagg aggaggaagt atgtgacccc aaattccatt atgacaacac agcaggaatc    3660
agtcagtatc tgcagaacag taagcgaaag agccggcctg tgagtgtaaa acatttgaa     3720 gatatcccgt tagaagaacc agaagtaaaa gtaatcccag atgacaacca gacggacagt     3780
ggtatggttc ttgcctcaga agagctgaaa actttggaag acagaaccaa attatctcca     3840
tcttttggtg aatggtgcc cagcaaaagc agggagtctg tggcatctga aggctcaaac     3900
```

| | | |
|---|---|---|
| cagacaagcg gctaccagtc cggatatcac tccgatgaca cagacaccac cgtgtactcc | 3960 |
| agtgaggaag cagaactttt aaagctgata gagattggag tgcaaaccgg tagcacagcc | 4020 |
| cagattctcc agcctgactc ggggaccaca ctgagctctc ctcctgttta a | 4071 |

<210> SEQ ID NO 3
<211> LENGTH: 7580
<212> TYPE: DNA
<213> ORGANISM: artificial sequence
<220> FEATURE:
<223> OTHER INFORMATION: sequence of expression vector pVAX10.VR2-1

<400> SEQUENCE: 3

| | |
|---|---|
| tgggcttttg ctggcctttt gctcacatgt tcttgactct tcgcgatgta cgggccagat | 60 |
| atacgcgttg acattgatta ttgactagtt attaatagta atcaattacg ggtcattag | 120 |
| ttcatagccc atatatggag ttccgcgtta cataacttac ggtaaatggc ccgcctggct | 180 |
| gaccgcccaa cgaccccgc ccattgacgt caataatgac gtatgttccc atagtaacgc | 240 |
| caatagggac tttccattga cgtcaatggg tggactattt acggtaaact gcccacttgg | 300 |
| cagtacatca agtgtatcat atgccaagta cgccccctat tgacgtcaat gacggtaaat | 360 |
| ggcccgcctg gcattatgcc cagtacatga ccttatggga ctttcctact ggcagtaca | 420 |
| tctacgtatt agtcatcgct attaccatgg tgatgcggtt ttggcagtac atcaatgggc | 480 |
| gtggatagcg gtttgactca cggggatttc caagtctcca ccccattgac gtcaatggga | 540 |
| gtttgttttg gcaccaaaat caacgggact ttccaaaatg tcgtaacaac tccgccccat | 600 |
| tgacgcaaat gggcggtagg cgtgtacggt gggaggtcta taagcagagc tctctggc | 660 |
| taactagaga acccactgct tactggctta tcgaaattaa tacgactcac tatagggaga | 720 |
| cccaagctgg ctagcaggat gcagagcaag gtgctgctgg ccgtcgccct gtggctctgc | 780 |
| gtggagcccc gggccgcctc tgtgggtttg cctagtgttt ctcttgatct gcccaggctc | 840 |
| agcatacaaa aagacatact tacaattaag gctaatacaa ctcttcaaat tacttgcagg | 900 |
| ggacagaggg acttggactg gctttggccc aataatcaga gtggcagtga gcaaagggtg | 960 |
| gaggtgactg agtgcagcga tggcctcttc tgtaagacac tcacaattcc aaaagtgatc | 1020 |
| ggaaatgaca ctggagccta caagtgcttc taccgggaaa ctgacttggc ctcggtcatt | 1080 |
| tatgtctatg ttcaagatta cagatctcca tttattgctt ctgttagtga ccaacatgga | 1140 |
| gtcgtgtaca ttactgagaa caaaaacaaa actgtggtga ttccatgtct cgggtccatt | 1200 |
| tcaaatctca acgtgtcact ttgtgcaaga tacccagaaa agagatttgt tcctgatggt | 1260 |
| aacagaattt cctgggacag caagaagggc tttactattc cagctacat gatcagctat | 1320 |
| gctggcatgg tcttctgtga agcaaaaatt aatgatgaaa gttaccagtc tattatgtac | 1380 |
| atagttgtcg ttgtaggta taggatttat gatgtggttc tgagtccgtc tcatggaatt | 1440 |
| gaactatctg ttggagaaaa gcttgtctta aattgtacag caagaactga actaaatgtg | 1500 |
| gggattgact tcaactggga ataccttct tcgaagcatc agcataagaa acttgtaaac | 1560 |
| cgagacctaa aaacccagtc tgggagtgag atgaagaaat tttgagcac cttaactata | 1620 |
| gatggtgtaa cccggagtga ccaaggattg tacacctgtg cagcatccag tgggctgatg | 1680 |
| accaagaaga acagcacatt tgtcagggtc catgaaaaac cttttgttgc ttttggaagt | 1740 |
| ggcatggaat ctctggtgga agccacggtg ggggagcgtg tcagaatccc tgcgaagtac | 1800 |
| cttggttacc caccccaga aataaaatgg tataaaaatg gaatacccct tgagtccaat | 1860 |
| cacacaatta agcggggca tgtactgacg attatggaag tgagtgaaag agacacagga | 1920 |

```
aattacactg tcatccttac caatcccatt tcaaaggaga agcagagcca tgtggtctct    1980
ctggttgtgt atgtcccacc ccagattggt gagaaatctc taatctctcc tgtggattcc    2040
taccagtacg gcaccactca aacgctgaca tgtacggtct atgccattcc tcccccgcat    2100
cacatccact ggtattggca gttggaggaa gagtgcgcca acgagcccag ccaagctgtc    2160
tcagtgacaa acccataccc ttgtgaagaa tggagaagtg tggaggactt ccagggagga    2220
aataaaattg aagttaataa aaatcaattt gctctaattg aaggaaaaaa caaaactgta    2280
agtacccttg ttatccaagc ggcaaatgtg tcagctttgt acaaatgtga agcggtcaac    2340
aaagtcggga gaggagagag ggtgatctcc ttccacgtga ccaggggtcc tgaaattact    2400
ttgcaacctg acatgcagcc cactgagcag gagagcgtgc ttttgtggtg cactgcagac    2460
agatctacgt ttgagaacct cacatggtac aagcttggcc cacagcctct gccaatccat    2520
gtgggagagt tgcccacacc tgttttgcaag aacttggata ctcttttggaa attgaatgcc    2580 accatgttct ctaatagcac aaatgacatt ttgatcatgg agcttaagaa tgcatccttg    2640
caggaccaag gagactatgt ctgccttgct caagacagga agaccaagaa aagacattgc    2700
gtggtcaggc agctcacagt cctagagcgt gtggcaccca cgatcacagg aaacctggag    2760
aatcagacga caagtattgg ggaaagcatc gaagtctcat gcacggcatc tgggaatccc    2820
cctccacaga tcatgtggtt taaagataat gagacccttg tagaagactc aggcattgta    2880
ttgaaggatg ggaaccggaa cctcactatc cgcagagtga ggaaggagga cgaaggcctc    2940
tacacctgcc aggcatgcag tgttcttggc tgtgcaaaag tggaggcatt tttcataata    3000
gaaggtgccc aggaaaagac gaacttggaa atcattattc tagtaggcac ggcggtgatt    3060
gccatgttct tctggctact tcttgtcatc atcctacgga ccgttaagcg ggccaatgga    3120
ggggaactga aagacaggcta cttgtccatc gtcatggatc cagatgaact cccattggat    3180
gaacattgtg aacgactgcc ttatgatgcc agcaaatggg aattccccag agaccggctg    3240
aagctaggta agcctcttgg ccgtggtgcc tttggccaag tgattgaagc agatgccttt    3300
ggaattgaca agacagcaac ttgcaggaca gtagcagtca aaatgttgaa agaaggagca    3360
acacacagtg agcatcgagc tctcatgtct gaactcaaga tcctcattca tattggtcac    3420
catctcaatg tggtcaacct tctaggtgcc tgtaccaagc aggagggcc actcatggtg    3480 attgtggaat ctgcaaatt tggaaacctg tccacttacc tgaggagcaa agaaaatgaa    3540 tttgtccct acaagaccaa aggggcacga ttccgtcaag ggaaagacta cgttggagca    3600
atccctgtgg atctgaaacg gcgcttggac agcatcacca gtagccagag ctcagccagc    3660
tctggatttg tggaggagaa gtccctcagt gatgtagaag aagaggaagc tcctgaagat    3720
ctgtataagg acttcctgac cttggagcat ctcatctgtt acagcttcca agtggctaag    3780
ggcatggagt tcttggcatc gcgaaagtgt atccacaggg acctggcggc acgaaatatc    3840
ctcttatcgg agaagaacgt ggttaaaatc tgtgactttg gcttggcccg ggatatttat    3900
aaagatccag attatgtcag aaaaggagat gctcgcctcc ctttgaaatg gatggcccca    3960
gaaacaattt ttgacagagt gtacacaatc cagagtgacg tctggtcttt tggtgttttg    4020
ctgtgggaaa tattttcctt aggtgcttct ccatatcctg gggtaaagat tgatgaagaa    4080
ttttgtaggc gattgaaaga aggaactaga atgagggccc ctgattatac tacaccagaa    4140
atgtaccaga ccatgctgga ctgctggcac ggggagccca gtcagagacc cacgtttttca    4200 gagttggtgg aacatttggg aaatctcttg caagctaatg ctcagcagga tggcaaagac    4260
tacattgttc ttccgatatc agagactttg agcatggaag aggattctgg actctctctg    4320
```

-continued

| | |
|---|---|
| cctacctcac ctgtttcctg tatggaggag gaggaagtat gtgaccccaa attccattat | 4380 |
| gacaacacag caggaatcag tcagtatctg cagaacagta agcgaaagag ccggcctgtg | 4440 |
| agtgtaaaaa catttgaaga tatcccgtta gaagaaccag aagtaaaagt aatcccagat | 4500 |
| gacaaccaga cggacagtgg tatggttctt gcctcagaag agctgaaaac tttggaagac | 4560 |
| agaaccaaat tatctccatc ttttggtgga atggtgccca gcaaaagcag ggagtctgtg | 4620 |
| gcatctgaag gctcaaacca gacaagcggc taccagtccg gatatcactc cgatgacaca | 4680 |
| gacaccaccg tgtactccag tgaggaagca gaacttttaa agctgataga gattggagtg | 4740 |
| caaaccggta gcacagccca gattctccag cctgactcgg ggaccacact gagctctcct | 4800 |
| cctgttttaaa aggaactcga gtctagaggg cccgtttaaa cccgctgatc agcctcgact | 4860 |
| gtgccttcta gttgccagcc atctgttgtt tgcccctccc ccgtgccttc cttgaccctg | 4920 |
| gaaggtgcca ctcccactgt cctttcctaa taaaatgagg aaattgcatc gcattgtctg | 4980 |
| agtaggtgtc attctattct ggggggtggg gtggggcagg acagcaaggg ggaggattgg | 5040 |
| gaagacaata gcaggcatgc tggggatgcg gtgggctcta tggcttctac tgggcggttt | 5100 |
| tatggacagc aagcgaaccg gaattgccag ctggggcgcc ctctggtaag gttgggaagc | 5160 |
| cctgcaaagt aaactggatg gctttctcgc cgccaaggat ctgatggcgc aggggatcaa | 5220 |
| gctctgatca agagacagga tgaggatcgt ttcgcatgat tgaacaagat ggattgcacg | 5280 |
| caggttctcc ggccgcttgg gtggagaggc tattcggcta tgactgggca acagacaa | 5340 |
| tcggctgctc tgatgccgcc gtgttccggc tgtcagcgca ggggcgcccg gttcttttg | 5400 |
| tcaagaccga cctgtccggt gccctgaatg aactgcaaga cgaggcagcg cggctatcgt | 5460 |
| ggctggccac gacgggcgtt ccttgcgcag ctgtgctcga cgttgtcact gaagcgggaa | 5520 |
| gggactggct gctattgggc gaagtgccgg ggcaggatct cctgtcatct caccttgctc | 5580 |
| ctgccgagaa agtatccatc atggctgatg caatgcggcg gctgcatacg cttgatccgg | 5640 |
| ctacctgccc attcgaccac caagcgaaac atcgcatcga gcgagcacgt actcggatgg | 5700 |
| aagccggtct tgtcgatcag gatgatctgg acgaagagca tcaggggctc gcgccagccg | 5760 |
| aactgttcgc caggctcaag gcgagcatgc ccgacggcga ggatctcgtc gtgacccatg | 5820 |
| gcgatgcctg cttgccgaat atcatggtgg aaaatggccg cttttctgga ttcatcgact | 5880 |
| gtggccggct gggtgtggcg gaccgctatc aggacatagc gttggctacc cgtgatattg | 5940 |
| ctgaagagct tggcggcgaa tgggctgacc gcttcctcgt gctttacggt atcgccgctc | 6000 |
| ccgattcgca gcgcatcgcc ttctatcgcc ttcttgacga gttcttctga attattaacg | 6060 |
| cttacaattt cctgatgcgg tatttttctcc ttacgcatct gtgcggtatt tcacaccgca | 6120 |
| tacaggtggc acttttcggg gaaatgtgcg cggaacccct atttgtttat ttttctaaat | 6180 |
| acattcaaat atgtatccgc tcatgagaca ataaccctga taaatgcttc aataatagca | 6240 |
| cgtgctaaaa cttcattttt aatttaaaag gatctaggtg aagatccttt ttgataatct | 6300 |
| catgaccaaa atcccttaac gtgagttttc gttccactga gcgtcagacc ccatcagtg | 6360 |
| accaaacagg aaaaaaccgc ccttaacatg gcccgcttta tcagaagcca gacattaacg | 6420 |
| cttctggaga aactcaacga gctggacgcg gatgaacagg cagacatctg tgaatcgctt | 6480 |
| cacgaccacg ctgatgagct ttaccgcagc tgcctcgcgc gtttcggtga tgacggtgaa | 6540 |
| aacctctgac acatgcagct cccggagacg gtcacagctt gtctgtaagc ggatgccggg | 6600 |
| agcagacaag cccgtcaggg cgcgtcagcg ggtgttggcg ggtgtcgggg cgcagccatg | 6660 |
| acccagtcac gtagcgatag cggagtgtat actggcttaa ctatgcggca tcagagcaga | 6720 |

```
ttgtactgag agtgcaccat atgcggtgtg aaataccgca cagatgcgta aggagaaaat    6780
accgcatcag gcgctcttcc gcttcctcgc tcactgactc gctgcgctcg gtcgttcggc    6840
tgcggcgagc ggtatcagct cactcaaagg cggtaatacg gttatccaca gaatcagggg    6900
ataacgcagg aaagaacatg tgagcaaaag gccagcaaaa ggccaggaac cgtaaaaagg    6960
ccgcgttgct ggcgtttttc cataggctcc gcccccctga cgagcatcac aaaaatcgac    7020
gctcaagtca gaggtggcga aacccgacag gactataaag ataccaggcg tttccccctg    7080
gaagctccct cgtgcgctct cctgttccga ccctgccgct taccggatac ctgtccgcct    7140
ttctcccttc gggaagcgtg gcgctttctc atagctcacg ctgtaggtat ctcagttcgg    7200
tgtaggtcgt tcgctccaag ctgggctgtg tgcacgaacc ccccgttcag cccgaccgct    7260
gcgccttatc cggtaactat cgtcttgagt ccaacccggt aagacacgac ttatcgccac    7320
tggcagcagc cactggtaac aggattagca gagcgaggta tgtaggcggt gctacagagt    7380
tcttgaagtg gtggcctaac tacggctaca ctagaaggac agtatttggt atctgcgctc    7440
tgctgaagcc agttaccttc ggaaaaagag ttggtagctc ttgatccggc aaacaaacca    7500
ccgctggtag cggtggtttt tttgtttgca agcagcagat tacgcgcaga aaaaaggat    7560 ctcaagaaga tcctttgatc                                               7580
```